United States Patent
Nakaie et al.

(10) Patent No.: US 9,780,309 B2
(45) Date of Patent: Oct. 3, 2017

(54) TRIPHENYLAMINE DERIVATIVE AND USE THEREFOR

(71) Applicant: NISSAN CHEMICAL INDUSTRIES, LTD., Tokyo (JP)

(72) Inventors: Naoki Nakaie, Funabashi (JP); Taichi Nakazawa, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/892,279

(22) PCT Filed: May 19, 2014

(86) PCT No.: PCT/JP2014/063198
§ 371 (c)(1),
(2) Date: Nov. 19, 2015

(87) PCT Pub. No.: WO2014/188998
PCT Pub. Date: Nov. 27, 2014

(65) Prior Publication Data
US 2016/0087220 A1 Mar. 24, 2016

(30) Foreign Application Priority Data
May 20, 2013 (JP) .................................. 2013-105854

(51) Int. Cl.
| C07C 209/68 | (2006.01) |
| C07C 211/54 | (2006.01) |
| H01L 51/00 | (2006.01) |
| H01L 51/50 | (2006.01) |
| H01L 51/52 | (2006.01) |

(52) U.S. Cl.
CPC ........ H01L 51/0059 (2013.01); C07C 209/68 (2013.01); C07C 211/54 (2013.01); H01L 51/0003 (2013.01); H01L 51/5088 (2013.01); H01L 51/5256 (2013.01)

(58) Field of Classification Search
CPC .......................... C07D 307/78; C07D 471/04
See application file for complete search history.

(56) References Cited

U.S. PATENT DOCUMENTS

2011/0108823 A1  5/2011  Stoessel et al.

FOREIGN PATENT DOCUMENTS

| JP | 2000-7625 A | 1/2000 |
| JP | 2002-151256 A | 5/2002 |
| JP | 2012-505168 A | 3/2012 |
| KR | 10-2012-0054938 A | 5/2012 |
| KR | 20120054938 | * 5/2012 |
| WO | WO 2006/025342 A1 | 3/2006 |
| WO | WO 2008/067276 A1 | 6/2008 |
| WO | WO 2008/129947 A1 | 10/2008 |
| WO | WO 2010/058777 A1 | 5/2010 |

OTHER PUBLICATIONS

English Translation of KR20120054938, May 2012, pp. 1-16.*
International Search Report for PCT/JP2014/063198 mailed on Aug. 12, 2014.
Written Opinion for PCT/JP2014/063198 mailed on Aug. 12, 2014.

* cited by examiner

Primary Examiner — Paul A Zucker
Assistant Examiner — Mark Luderer
(74) Attorney, Agent, or Firm — Birch, Stewart, Kolasch & Birch, LLP

(57) ABSTRACT

A triphenylamine derivative represented by formula (1) exhibits good solubility in an organic solvent and allows an organic EL element having excellent luminance characteristics to be achieved when formed into a thin film and applied to a positive hole injection layer.

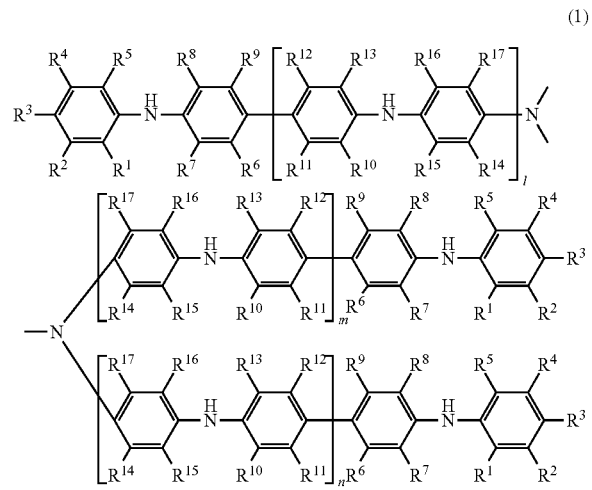

(1)

(In the formula, $R^1$ to $R^{17}$ mutually independently represent a hydrogen atom, a halogen atom, a nitro group, a cyano group, an amino group, an aldehyde group, a hydroxyl group, a thiol group, a carboxylic acid group, and the like; and l, m, and n mutually independently represent an integer 1 to 5.)

10 Claims, No Drawings

TRIPHENYLAMINE DERIVATIVE AND USE THEREFOR

TECHNICAL FIELD

The present invention relates to triphenylamine derivatives and to the use thereof. More specifically, the invention relates to triphenylamine derivatives having diphenylamine skeletons as recurring units, and to their use as charge-transporting substances.

BACKGROUND ART

Charge-transporting thin-films made of organic compounds are used as emissive layers and charge injection layers in organic electroluminescence (organic EL) devices. In particular, a hole injection layer is responsible for transferring charge between a positive electrode and a hole transport layer or an emissive layer, and thus serves an important function in achieving low-voltage driving and high brightness in organic EL devices.

Processes for forming the hole injection layer are broadly divided into dry processes such as vapor deposition and wet processes such as spin coating. On comparing dry processes and wet processes, the latter are capable of efficiently producing thin-films having a high flatness over a large surface area. Hence, with the advances being made today toward organic EL displays of larger surface area, there exists a desire for hole injection layers that can be formed by wet processes.

In view of these circumstances, the inventors have developed charge-transporting materials which may be employed in various types of wet processes and which, when used as hole injection layers for organic EL devices, are capable of achieving excellent EL device characteristics. The inventors have also developed compounds of good solubility in organic solvents for use in such charge-transporting materials (see, for example, Patent Documents 1 to 4).

PRIOR ART DOCUMENTS

Patent Documents

Patent Document 1: WO 2008/067276
Patent Document 2: WO 2008/129947
Patent Document 3: WO 2006/025342
Patent Document 4: WO 2010/058777

SUMMARY OF THE INVENTION

Problems to be Solved by the Invention

It is therefore an object of this invention to provide a triphenylamine derivative which, as with the art in the above patent publications that has been developed to date, exhibits good solubility in organic solvents and, when formed into a thin-film and used as a hole injection layer, enables organic EL devices endowed with excellent brightness characteristics to be achieved.

Means for Solving the Problems

The inventors have conducted extensive investigations, as a result of which they have discovered that triphenylamine derivatives having diphenylamine skeletons as recurring units exhibit a high solubility in organic solvents. They have also found that thin-films obtained from varnishes prepared by dissolving such triphenylamine derivatives together with a dopant substance in an organic solvent have high charge-transporting properties and, when used as a hole injection layer, are capable of achieving excellent brightness characteristics.

Accordingly, the invention provides:
1. A triphenylamine derivative characterized by having formula (1)

[Chemical Formula 1]

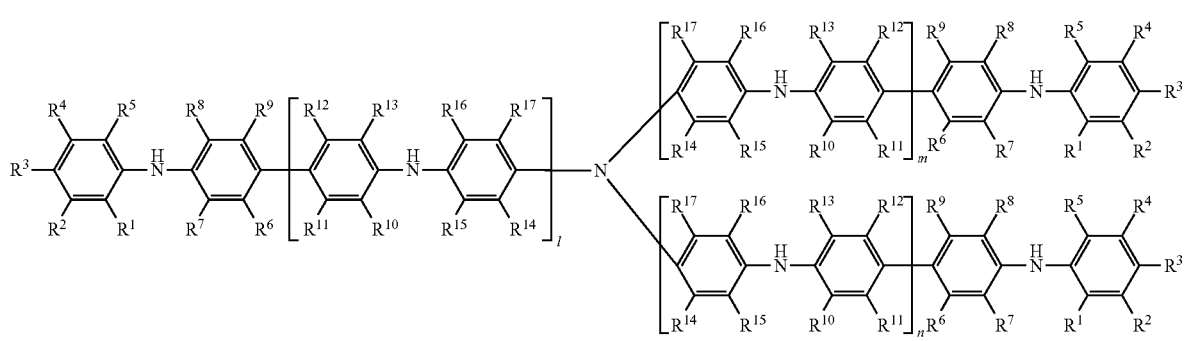

(1)

(wherein $R^1$ to $R^{17}$ are each independently a hydrogen atom, a halogen atom, a nitro group, a cyano group, an amino group, an aldehyde group, a hydroxyl group, a thiol group, a carboxyl group, an alkyl group of 1 to 20 carbons which may be substituted with $Z^1$, an alkenyl group of 2 to 20 carbons which may be substituted with $Z^1$, an alkynyl group of 2 to 20 carbons which may be substituted with $Z^1$, an aryl group of 6 to 20 carbons which may be substituted with $Z^2$, a heteroaryl group of 2 to 20 carbons which may be substituted with $Z^2$, $-NHY^1$, $-NY^2Y^3$, $-C(O)Y^4$, $-OY^5$, $-SY^6$, $-C(O)OY^7$, $-OC(O)Y^8$, $-C(O)NHY^9$ or $-C(O)NY^{10}Y^{11}$, $Y^1$ to $Y^{11}$ are each independently an alkyl group of 1 to 20 carbons which may be substituted with $Z^1$, an alkenyl group of 2 to 20 carbons which may be substituted with $Z^1$, an alkynyl group of 2 to 20 carbons which may be substituted with $Z^1$, an aryl group of 6 to 20 carbons which may be substituted with $Z^2$, or a heteroaryl group of 2 to 20 carbons which may be substituted with $Z^2$, in which $Z^1$ is a halogen atom, a nitro group, a cyano group, an amino group, an aldehyde group, a hydroxyl group, a thiol group, a sulfonic acid group, a carboxyl group, an aryl group of 6 to 20 carbons which may be substituted with $Z^3$, or a heteroaryl group of 2 to 20 carbons which may be substituted with $Z^3$;

$Z^2$ is a halogen atom, a nitro group, a cyano group, an amino group, an aldehyde group, a hydroxyl group, a thiol group, a sulfonic acid group, a carboxyl group, an alkyl group of 1 to 20 carbons which may be substituted with $Z^3$, an alkenyl group of 2 to 20 carbons which may be substituted with $Z^3$, or an alkynyl group of 2 to 20 carbons which may be substituted with $Z^3$; and $Z^3$ is a halogen atom, a nitro group, a cyano group, an amino group, an aldehyde group, a hydroxyl group, a thiol group, a sulfonic acid group or a carboxyl group; and the letters l, m and n are each independently integers from 1 to 5);

2. The triphenylamine derivative of 1 above, wherein $R^1$ to $R^{17}$ are all hydrogen atoms;

3. A charge-transporting substance consisting of the triphenylamine derivative of 1 or 2 above;

4. A charge-transporting material which includes charge-transporting substance of 3 above;

5. A charge-transporting varnish which includes the charge-transporting substance of 3 above, a dopant substance and an organic solvent;

6. A charge-transporting thin-film produced using the charge-transporting varnish of 5 above;

7. An electronic device which includes the charge-transporting thin-film of 6 above;

8. An organic electroluminescence device which includes the charge-transporting thin-film of 6 above;

9. A method of producing a charge-transporting thin-film, characterized by coating the charge-transporting varnish of 5 above onto a substrate and evaporating off the solvent;

10. A method of producing the triphenylamine derivative of 1 above, which method includes the step of reacting the triphenylamine compound of formula (2) with compounds having the diphenylamine structures of formulas (3) to (5)

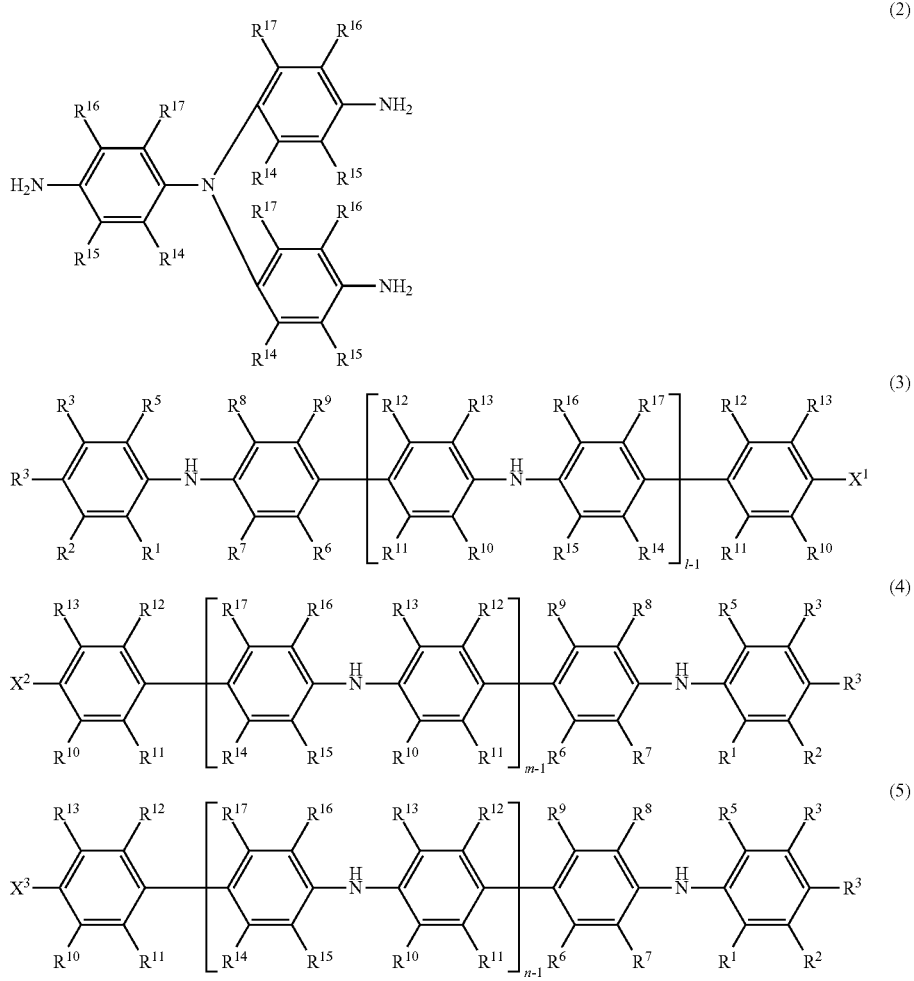

(wherein $X^1$ to $X^3$ are each independently a halogen atom or a pseudo-halogen group, and $R^3$ to $R^{17}$ and the letters l, m and n are as defined above)

in the presence of a catalyst.

Advantageous Effects of the Invention

The triphenylamine derivative of the invention is readily soluble in organic solvents, and a charge-transporting varnish can easily be prepared by dissolving this together with a dopant substance in an organic solvent.

Thin-films produced from the charge-transporting varnish of the invention exhibit high charge-transporting properties, and can thus be advantageously used as thin-films for organic EL devices and other electronic devices. In particular, by employing such a thin-film as a hole injection layer in an organic EL device, it is possible to obtain organic EL devices having excellent brightness characteristics.

Also, the charge-transporting varnish of the invention can reproducibly produce thin-films of excellent charge transportability even using various wet processes capable of film formation over a large surface area, such as spin coating or slit coating, and is thus capable of fully accommodating recent advances in the field of organic EL devices.

EMBODIMENT FOR CARRYING OUT THE INVENTION

The invention is described more fully below.
The triphenylamine derivative according to this invention has formula (1).

[Chemical Formula 3]

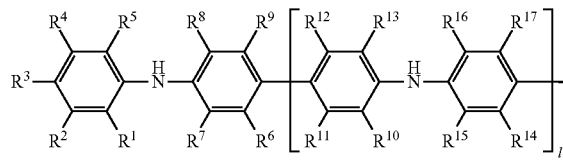
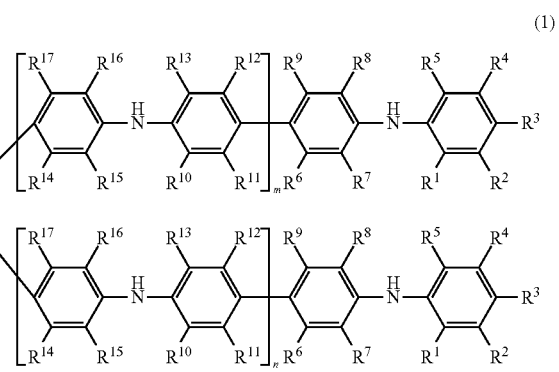

(1)

In formula (1), $R^1$ to $R^{17}$ are each independently a hydrogen atom, a halogen atom, a nitro group, a cyano group, an amino group, an aldehyde group, a hydroxyl group, a thiol group, a carboxyl group, an alkyl group of 1 to 20 carbons which may be substituted with $Z^1$, an alkenyl group of 2 to 20 carbons which may be substituted with $Z^1$, an alkynyl group of 2 to 20 carbons which may be substituted with $Z^1$, an aryl group of 6 to 20 carbons which may be substituted with $Z^2$, a heteroaryl group of 2 to 20 carbons which may be substituted with $Z^2$, $-NHY^1$, $-NY^2Y^3$, $-C(O)Y^4$, $-OY^5$, $-SY^6$, $-C(O)OY^7$, $-OC(O)Y^8$, $-C(O)NHY^9$ or $-C(O)NY^{10}Y^{11}$. Here, $Y^1$ to $Y^{11}$ are each independently an alkyl group of 1 to 20 carbons which may be substituted with $Z^1$, an alkenyl group of 2 to 20 carbons which may be substituted with $Z^1$, alkynyl group of 2 to 20 carbons which may be substituted with $Z^1$, an aryl group of 6 to 20 carbons which may be substituted with $Z^2$, or a heteroaryl group of 2 to 20 carbons which may be substituted with $Z^2$.

Of the plurality $R^n$ (where n=1 to 17) of R moieties present, all may be of the same type, all may be of different types, any two or more may be of the same type with the remainder being of different types, or any two or more may be of the same type with the remaining two or more being of a same type differing from the first type.

Examples of the halogen atom include fluorine, chlorine, bromine and iodine atoms.

The alkyl group of 1 to 20 carbons may be linear, branched or cyclic, and is exemplified by linear or branched alkyl groups of 1 to 20 carbons such as methyl, ethyl, n-propyl, isopropyl, n-butyl, isobutyl, s-butyl, t-butyl, n-pentyl, n-hexyl, n-heptyl, n-octyl, n-nonyl and n-decyl groups; and cyclic alkyl groups of 3 to 20 carbons such as cyclopropyl, cyclobutyl, cyclopentyl, cyclohexyl, cycloheptyl, cyclooctyl, cyclononyl, cyclodecyl, bicyclobutyl, bicyclopentyl, bicyclohexyl, bicycloheptyl, bicyclooctyl, bicyclononyl and bicyclodecyl groups.

Examples of alkenyl groups of 2 to 20 carbons include ethenyl, n-1-propenyl, n-2-propenyl, 1-methylethenyl, n-1-butenyl, n-2-butenyl, n-3-butenyl, 2-methyl-1-propenyl, 2-methyl-2-propenyl, 1-ethylethenyl, 1-methyl-1-propenyl, 1-methyl-2-propenyl, n-1-pentenyl, n-1-decenyl and n-1-eicosenyl groups.

Examples of alkynyl groups of 2 to 20 carbons include ethynyl, n-1-propynyl, n-2-propynyl, n-1-butynyl, n-2-butynyl, n-3-butynyl, 1-methyl-2-propynyl, n-1-pentynyl, n-2-pentynyl, n-3-pentynyl, n-4-pentynyl, 1-methyl-n-butynyl, 2-methyl-n-butynyl, 3-methyl-n-butynyl, 1,1-dimethyl-n-propynyl, n-1-hexynyl, n-1-decynyl, n-1-pentadecynyl and n-1-eicosynyl groups.

Examples of aryl groups of 6 to 20 carbons include phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl groups.

Examples of heteroaryl groups of 2 to 20 carbons include 2-thienyl, 3-thienyl, 2-furanyl, 3-furanyl, 2-oxazolyl, 4-oxazolyl, 5-oxazolyl, 3-isooxazolyl, 4-isooxazolyl, 5-isooxazolyl, 2-thiazolyl, 4-thiazolyl, 5-thiazolyl, 3-isothiazolyl, 4-isothiazolyl, 5-isothiazolyl, 2-imidazolyl, 4-imidazolyl, 2-pyridyl, 3-pyridyl and 4-pyridyl groups.

Of these, $R^1$ to $R^{17}$ are preferably hydrogen atoms, fluorine atoms, cyano groups, alkyl groups of 1 to 20 carbons which may be substituted with $Z^1$, aryl groups of 6 to 20 carbons which may be substituted with $Z^2$, $-NHY^1$ in which $Y^1$ is an aryl group of 6 to 20 carbons which may be substituted with $Z^2$, or $-NY^2Y^3$ in which $Y^2$ and $Y^3$ are aryl groups of 6 to 20 carbons which may be substituted with $Z^2$; more preferably hydrogen atoms, fluorine atoms, cyano groups, alkyl groups of 1 to 10 carbons which may be substituted with $Z^1$, phenyl groups which may be substituted with $Z^2$, diphenylamino groups which may be substituted with $Z^2$, or phenylamino groups which may be substituted with $Z^2$; even more preferably hydrogen atoms, fluorine atoms, phenyl groups which may be substituted with $Z^2$, or diphenylamino groups which may be substituted with $Z^2$; and most preferably hydrogen atoms.

The letters l, m and n are each independently integers from 1 to 5. Taking into consideration the solubility in organic solvents, they are preferably integers which satisfy the condition $3 \leq l+m+n \leq 8$, more preferably integers which satisfy the condition $3 \leq l+m+n \leq 6$, even more preferably integers which satisfy the condition $3 \leq l+m+n \leq 4$, and most preferably $l+m+n=3$.

The alkyl groups, alkenyl groups and alkynyl groups of $R^1$ to $R^{17}$ and $Y^1$ to $Y^{11}$ may be substituted with $Z^1$, which is a halogen atom, a nitro group, a cyano group, an amino group, an aldehyde group, a hydroxyl group, a thiol group, a sulfonic acid group, a carboxyl group, an aryl group of 6 to 20 carbons which may be substituted with $Z^3$, or a heteroaryl group of 2 to 20 carbons which may be substituted with $Z^3$. The aryl groups and heteroaryl groups of $R^1$ to $R^{17}$ and $Y^1$ to $Y^{11}$ may be substituted with $Z^2$, which is a halogen atom, a nitro group, a cyano group, an amino group, an aldehyde group, a hydroxyl group, a thiol group, a sulfonic acid group, a carboxyl group, an alkyl group of 1 to 20 carbons which may be substituted with $Z^3$, an alkenyl group of 2 to 20 carbons which may be substituted with $Z^3$, or an alkynyl group of 2 to 20 carbons which may be substituted with $Z^3$. These groups may in turn be substituted with $Z^3$, which is a halogen atom, a nitro group, a cyano group, an amino group, an aldehyde group, a hydroxyl group, a thiol group, a sulfonic acid group or a carboxyl group (the halogen atoms being exemplified as indicated above).

Notably, in $R^1$ to $R^{17}$ and $Y^1$ to $Y^{11}$, the substituent $Z^1$ is preferably a halogen atom or an aryl group of 6 to 20 carbons which may be substituted with $Z^3$, more preferably a halogen atom or a phenyl group which may be substituted with $Z^3$, and most preferably does not exist (i.e., is non-substituting).

Also, the substituent $Z^2$ is preferably a halogen atom or an alkyl group of 1 to 20 carbons which may be substituted with $Z^3$, more preferably a halogen atom or an alkyl group of 1 to 4 carbons which may be substituted with $Z^3$, and most preferably does not exist (i.e., is non-substituting).

$Z^3$ is preferably a halogen atom, more preferably fluorine, and most preferably does not exist (i.e., is non-substituting).

In $R^1$ to $R^{17}$ and $Y^1$ to $Y^{11}$, the number of carbons on the alkyl, alkenyl and alkynyl groups is preferably 10 or less, more preferably 6 or less, and even more preferably 4 or less.

The number of carbons on the aryl and heteroaryl groups is preferably 14 or less, more preferably 10 or less, and even more preferably 6 or less.

The triphenylamine derivative of the invention may be prepared by reacting a triphenylamine compound of formula (2) with compounds having the diphenylamine structures of formulas (3) to (5) in the presence of a catalyst.

[Chemical Formula 4]

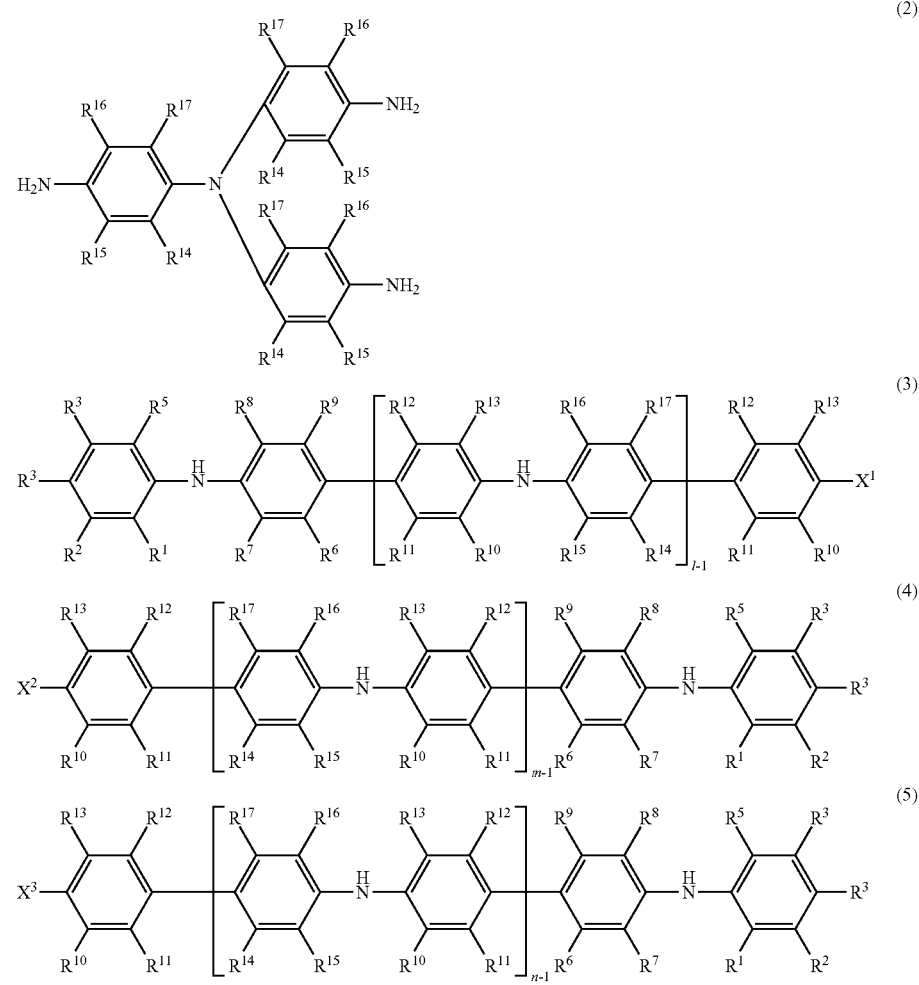

(In the formulas, $X^1$ to $X^3$ are each independently a halogen atom or a pseudo-halogen group, and $R^1$ to $R^{17}$ and the letters l, m and n are as defined above.)

The halogen atom is exemplified in the same way as above.

The pseudo-halogen group is exemplified by (fluoro)alkylsulfonyloxy groups such as methanesulfonyloxy, trifluoromethanesulfonyloxy and nanofluorobutanesulfonyloxy groups; and aromatic sulfonyloxy groups such as benzenesulfonyloxy and toluenesulfonyloxy groups.

The amine compound of formula (2) is exemplified by, but not limited to, tris(4-aminophenyl)amine. The compounds having diphenylamine structures of formulas (3) to (5) are exemplified by, but not limited to, 4'-bromo-N-phenyl-[1,1'-biphenyl]-4-amine.

The charging ratio of the triphenylamine compound of formula (2) and the compounds having diphenylamine structures of formulas (3) to (5) may be set to 1 equivalent or more, and preferably from about 1 to about 1.2 equivalents, of each compound having the diphenylamine structures of formulas (3) to (5) per mole of the triphenylamine compound.

The catalyst used in this reaction is exemplified by copper catalysts such as copper chloride, copper bromide and copper iodide; and palladium catalysts such as $Pd(PPh_3)_4$ (tetrakis(triphenylphosphine)palladium), $Pd(PPh_3)_2Cl_2$ (bis(triphenylphosphine)dichloropalladium), $Pd(dba)_2$ (bis(benzylideneacetone)palladium), $Pd_2(dba)_3$ (tris(benzylideneacetone)dipalladium) and $Pd(P-t-Bu_3)_2$ (bis(tri(t-butyl)phosphine)palladium). These catalysts may be used singly or two or more may be used in combination. Also, these catalysts may be used together with suitable known ligands.

The amount of catalyst used may be set to about 0.2 mole per mole of the triphenylamine compound of formula (2), with an amount of about 0.15 mole being preferred.

When ligands are used, the amount of ligands may be set to from 0.1 to 5 equivalents, and preferably from 1 to 2 equivalents, with respect to the metal complex used.

The above reaction may be carried out in a solvent. When using a solvent, the type of solvent is not particularly limited, provided it is one that does not adversely affect the reaction. Illustrative examples include aliphatic hydrocarbons (pentane, n-hexane, n-octane, n-decane, decalin, etc.), halogenated aliphatic hydrocarbons (chloroform, dichloromethane, dichloroethane, carbon tetrachloride, etc.), aromatic hydrocarbons (benzene, nitrobenzene, toluene, o-xylene, m-xylene, p-xylene, mesitylene, etc.), halogenated aromatic hydrocarbons (chlorobenzene, bromobenzene, o-dichlorobenzene, m-dichlorobenzene, p-dichlorobenzene, etc.), ethers (diethyl ether, diisopropyl ether, t-butyl methyl ether, tetrahydrofuran, dioxane, 1,2-dimethoxyethane, 1,2-diethoxyethane, etc.), ketones (acetone, methyl ethyl ketone, methyl isobutyl ketone, di-n-butyl ketone, cyclohexanone, etc.), amides (N,N-dimethylformamide, N,N-dimethylacetamide, etc.), lactams and lactones (N-methylpyrrolidone, γ-butyrolactone, etc.), ureas (N,N-dimethylimidazolidinone, tetramethylurea, etc.), sulfoxides (dimethylsulfoxide, sulfolane, etc.) and nitriles (acetonitrile, propionitrile, butyronitrile, etc.). These solvents may be used singly, or two or more may be used in admixture.

The reaction temperature may be suitably set in the range of from the melting point to the boiling point of the solvent used, with a temperature of from about 0° C. to about 200° C. being preferred, and a temperature of 20 to 150° C. being more preferred.

The target triphenylamine derivative can be obtained by work-up in the usual manner following reaction completion.

Examples of the triphenylamine derivative of formula (1) include, but are not limited to, the following.

[Chemical Formula 5]

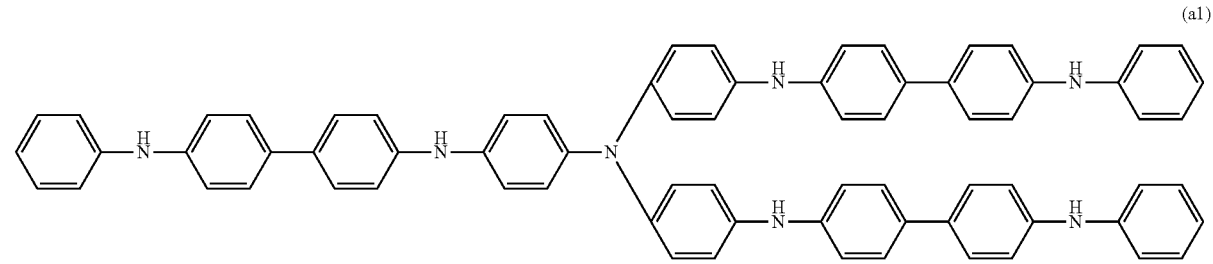

(a1)

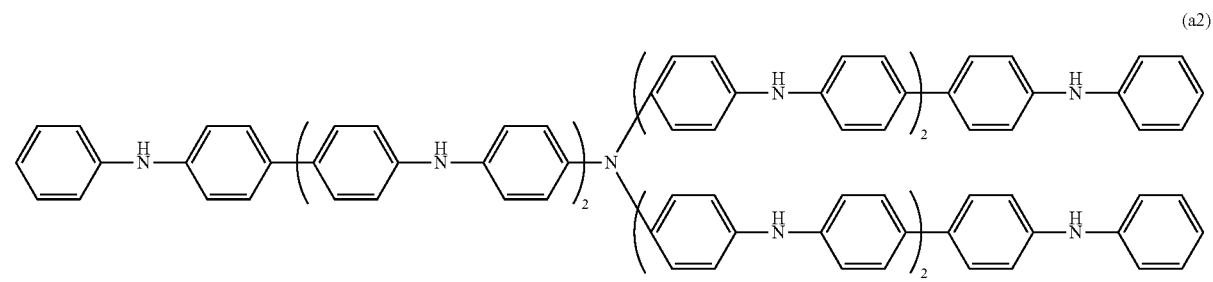

(a2)

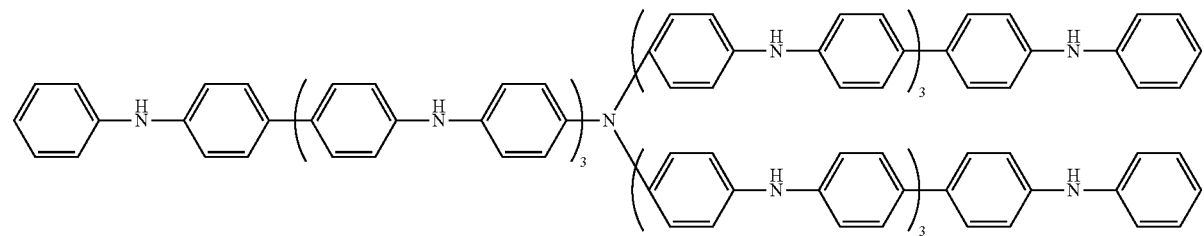
(a3)
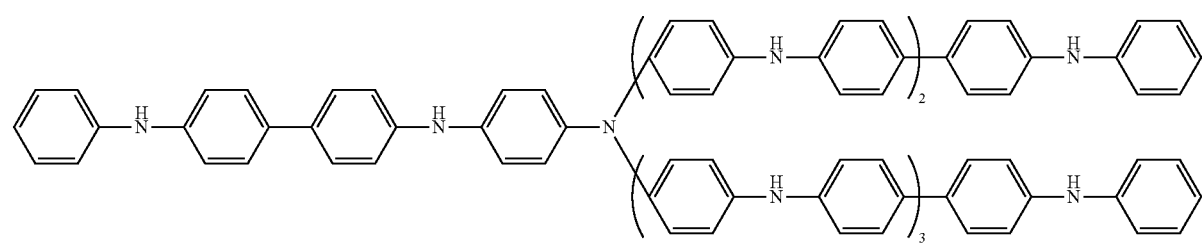
(a4)
[Chemical Formula 6]
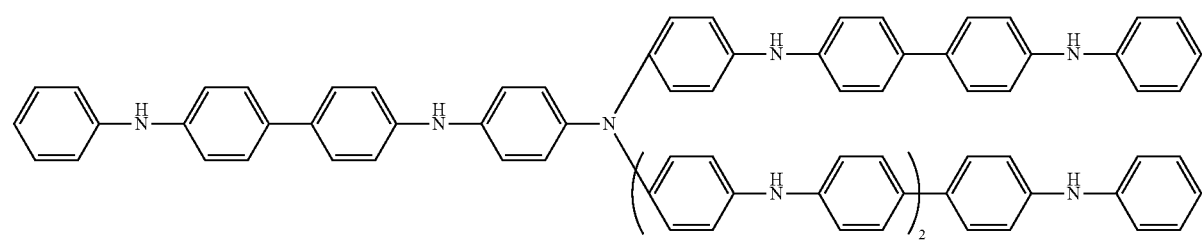
(a5)
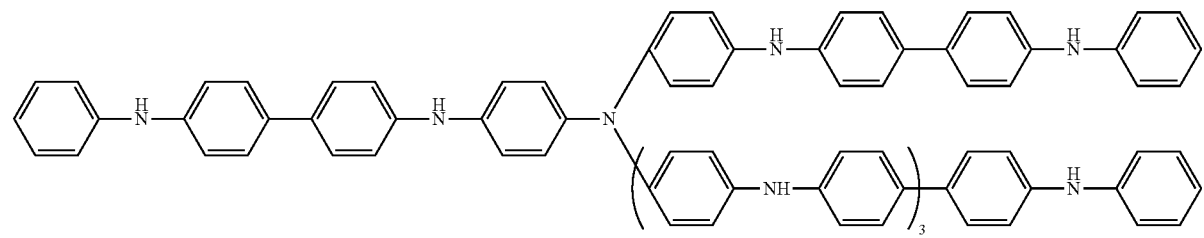
(a6)
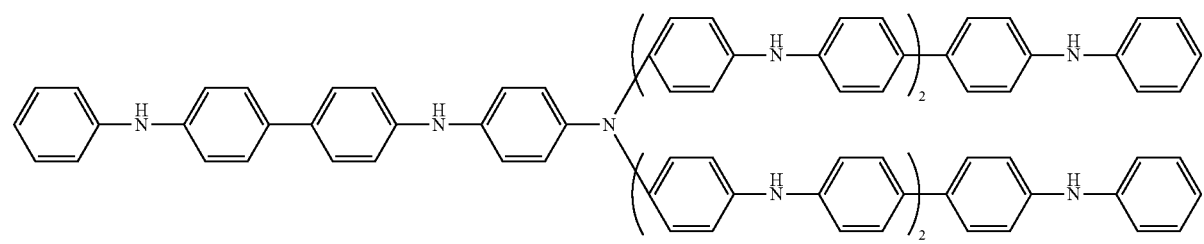
(a7)

(a8)
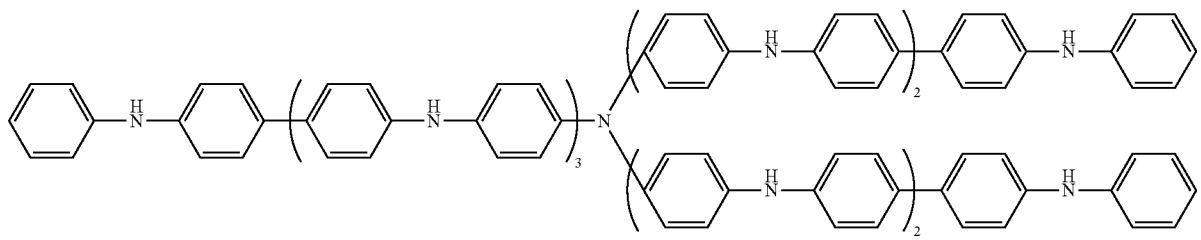

(a9)
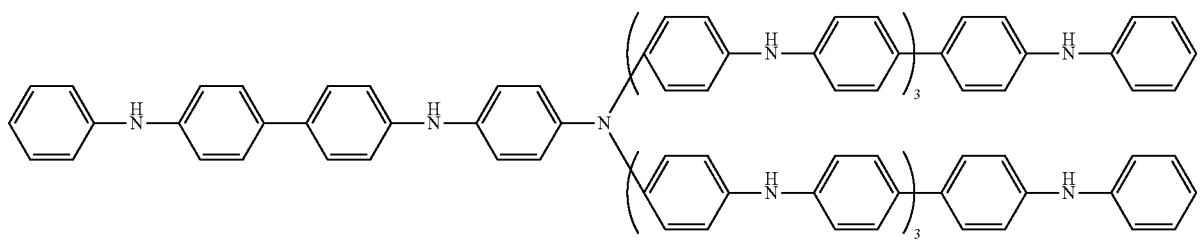

(a10)
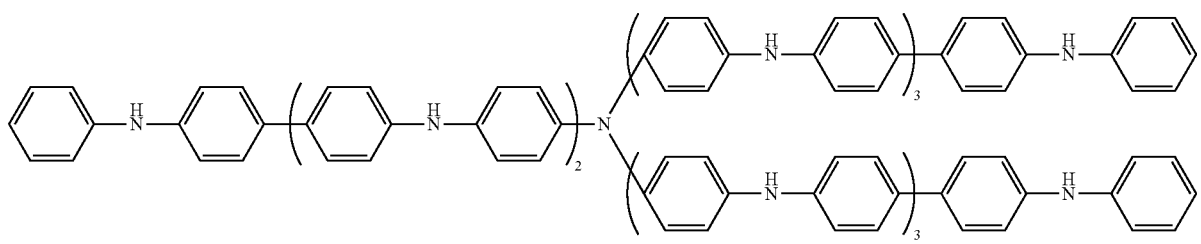

The charge-transporting varnish of the invention includes a charge-transporting substance consisting of the triphenylamine derivative of formula (1) and an organic solvent, and may optionally include also a dopant substance so as to enhance, for example, the charge transportability, etc.

The dopant substance is not particularly limited, provided it dissolves in at least one solvent used in the varnish; either an inorganic dopant substance or an organic dopant substance may be used.

Examples of inorganic dopant substances include inorganic acids such as hydrogen chloride, sulfuric acid, nitric acid and phosphoric acid; metal halides such as aluminum (III) chloride ($AlCl_3$), titanium(IV) tetrachloride ($TiCl_4$), boron tribromide ($BBr_3$), boron trifluoride-ether complex ($BF_3 \cdot OEt_2$), iron(III) chloride ($FeCl_3$), copper(II) chloride ($CuCl_2$), antimony(V) pentachloride ($SbCl_5$), antimony(V) pentafluoride ($SbF_5$), arsenic(V) pentafluoride ($AsF_5$), phosphorus pentafluoride ($PF_5$) and tris(4-bromophenyl)aluminum hexachloroantimonate (TBPAH); halogens such as $Cl_2$, $Br_2$, $I_2$, ICl, $ICl_3$, IBr and $IF_4$; and heteropolyacids such as phosphomolybdic acid and phosphotungstic acid.

Examples of organic dopant substances include aryl sulfone compounds such as benzenesulfonic acid, tosylic acid, p-styrenesulfonic acid, 2-naphthalenesulfonic acid, 4-hydroxybenzenesulfonic acid, 5-sulfosalicyclic acid, p-dodecylbenzenesulfonic acid, dihexylbenzenesulfonic acid, 2,5-dihexylbenzenesulfonic acid, dibutylnaphthalenesulfonic acid, 6,7-dibutyl-2-naphthalenesulfonic acid, dodecylnaphthalenesulfonic acid, 3-dodecyl-2-naphthalenesulfonic acid, hexylnaphthalenesulfonic acid, 4-hexyl-1-naphthalenesulfonic acid, octylnaphthalenesulfonic acid, 2-octyl-1-naphthalenesulfonic acid, hexylnaphthalenesulfonic acid, 7-hexyl-1-naphthalenesulfonic acid, 6-hexyl-2-naphthalenesulfonic acid, dinonylnaphthalenesulfonic acid, 2,7-dinonyl-4-naphthalenesulfonic acid, dinonylnaphthalenedisulfonic acid, 2,7-dinonyl-4,5-naphthalenedisulfonic acid, the 1,4-benzodioxanedisulfonic acid compounds mentioned in International Disclosure WO 2005/000832, the arylsulfonic acid compounds mentioned in International Disclosure WO 2006/025342, the arylsulfonic acid compounds mentioned in International Disclosure WO 2009/096352 and polystyrenesulfonic acid; non-aryl sulfone compounds such as 10-camphorsulfonic acid; and organic oxidizing agents such as 7,7,8,8-tetracyanoquinodimethane (TCNQ) and 2,3-dichloro-5,6-dicyano-1,4-benzoquinone (DDQ).

These inorganic and organic dopant substances may be used singly, or two or more may be used in combination.

Of these dopant substances, a heteropolyacid is preferred. By using a heteropolyacid as the dopant substance, it is possible to obtain a thin-film of excellent charge transportability that not only has a high hole-accepting ability from transparent electrodes such as indium-tin oxide (ITO) or indium-zinc oxide (IZO), but also exhibits a high hole-accepting ability from metal positive electrodes such as aluminum.

"Heteropolyacid" refers to a polyacid having a structure in which a heteroatom is positioned at the center of the molecule—typically the Keggin-type chemical structure or the Dawson-type chemical structure, and which is obtained by the condensation of an isopolyacid which is an oxo acid of vanadium (V), molybdenum (Mo), tungsten (W) or the like with an oxo acid of a different element. Examples of this oxo acid of another element include primarily oxo acids of silicon (Si), phosphorus (P) and arsenic (As).

Examples of heteropolyacids include phosphomolybdic acid, silicomolybdic acid, phosphotungstic acid, silicotungstic acid and phosphotungstomolybdic acid. These may be used singly, or two or more may be used in combination. The heteropolyacid compound used in this invention may be acquired as a commercial product or may be synthesized by a known method.

In cases where the dopant substance is composed of a single heteropolyacid by itself, this one heteropolyacid is preferably phosphotungstic acid or phosphomolybdic acid, and is most preferably phosphotungstic acid. In cases where the dopant substance is composed of two or more heteropolyacids, at least one of the two or more heteropolyacids is preferably phosphotungstic acid or phosphomolybdic acid, and is more preferably phosphotungstic acid.

Even a heteropolyacid for which, in quantitative analysis such as elemental analysis, the number for an element is higher or lower than in the structure indicated by the general formula may be used in this invention, provided it was acquired as a commercial product or was suitably synthesized according to a publicly known method of synthesis.

Thus, for example, phosphotungstic acid is generally represented by the chemical formula $H_3(PW_{12}O_{40}) \cdot nH_2O$ and phosphomolybdic acid is generally represented by the chemical formula $H_3(PMo_{12}O_{40}) \cdot nH_2O$. In quantitative analysis, regardless of whether the numbers for the elements P (phosphorus), O (oxygen) and W (tungsten) or Mo (molybdenum) within these formulas are high or low, so long as the heteropolyacid was acquired as a commercial product or suitably synthesized by a publicly known method of synthesis, it may be used in this invention. In such cases, the weight of the heteropolyacid specified in this invention refers not to the weight of, for example, pure phosphotungstic acid (phosphotungstic acid content) within the product of synthesis or the commercial product, but rather, in the form available as a commercial product or the form that can be isolated by a publicly known method of synthesis, to the total weight in a state that includes water of hydration and other impurities.

An arylsulfonic acid compound may also be advantageously used as the dopant substance. Arylsulfonic acid compounds of formula (6) or (7) are especially preferred.

[Chemical Formula 8]

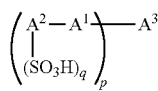

(6)

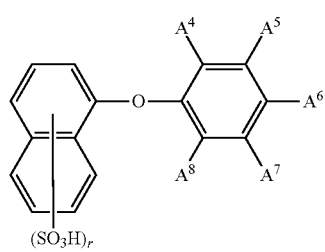

(7)

Here, $A^1$ is oxygen or sulfur, with oxygen being preferred.

$A^2$ is a naphthalene ring or an anthracene ring, with a naphthalene ring being preferred.

$A^3$ is a perfluorobiphenyl group having a valence of 2 to 4. The letter p represents the number of bonds between $A^1$ and $A^3$. This is an integer which satisfies the condition $2 \leq p \leq 4$. $A^3$ is preferably a divalent perfluorobiphenyl group, and p is preferably 2.

The letter q represents the number of sulfonic acid groups that bond to $A^2$. This is an integer which satisfies the condition $1 \leq q \leq 4$, and is most preferably 2.

$A^4$ to $A^8$ are each independently a hydrogen atom, a halogen atom, a cyano group, an alkyl group of 1 to 20 carbons, a halogenated alkyl group of 1 to 20 carbons or a halogenated alkenyl group of 2 to 20 carbons, with at least 3 of $A^4$ to $A^8$ being halogen atoms.

Examples of the halogenated alkyl group of 1 to 20 carbons include trifluoromethyl, 2,2,2-trifluoroethyl, 1,1,2,2,2-pentafluoroethyl, 3,3,3-trifluoropropyl, 2,2,3,3,3-pentafluoropropyl, 1,1,2,2,3,3,3-heptafluoropropyl, 4,4,4-trifluorobutyl, 3,3,4,4,4-pentafluorobutyl, 2,2,3,3,4,4,4-heptafluorobutyl and 1,1,2,2,3,3,4,4,4-nonafluorobutyl groups.

Examples of the halogenated alkenyl group of 2 to 20 carbons include perfluorovinyl, perfluoropropenyl (allyl) and perfluorobutenyl groups.

In addition, the halogen atom and the alkyl group of 1 to 20 carbons are exemplified in the same way as above. The halogen atom is preferably a fluorine atom.

Of these, $A^4$ to $A^8$ are preferably hydrogen atoms, halogen atoms, cyano groups, alkyl groups of 1 to 10 carbons, halogenated alkyl groups of 1 to 10 carbons, or halogenated alkenyl groups of 2 to 10 carbons, with at least 3 of $A^4$ to $A^8$ being fluorine atoms; more preferably hydrogen atoms, fluorine atoms, cyano groups, alkyl groups of 1 to 5 carbons, fluorinated alkyl groups of 1 to 5 carbons, or fluorinated alkenyl groups of 2 to 5 carbons, with at least 3 of $A^4$ to $A^8$ being fluorine atoms; and even more preferably hydrogen atoms, fluorine atoms, cyano groups, perfluoroalkyl groups of 1 to 5 carbons, or perfluoroalkenyl groups of 1 to 5 carbons, with $A^4$, $A^5$ and $A^8$ being fluorine atoms.

Here, "perfluoroalkyl group" refers to an alkyl group in which all the hydrogen atoms are substituted with fluorine atoms, and "perfluoroalkenyl group" refers to an alkenyl group in which all the hydrogen atoms are substituted with fluorine atoms.

The letter r represents the number of sulfonic acid groups that bond to the naphthalene ring. This is an integer which satisfies the condition $1 \leq r \leq 4$, is preferably from 2 to 4, and is most preferably 2.

The molecular weight of the arylsulfonic acid compound used as the dopant substance is not particularly limited. However, taking into consideration the solubility in an organic solvent in cases where it is used together with the triphenylamine derivative of formula (1), the molecular weight is preferably not more than 2,000, and more preferably not more than 1,500.

In this invention, examples of arylsulfonic acid compounds that are preferred as the dopant substance include, but are not limited to, the following.

[Chemical Formula 9]

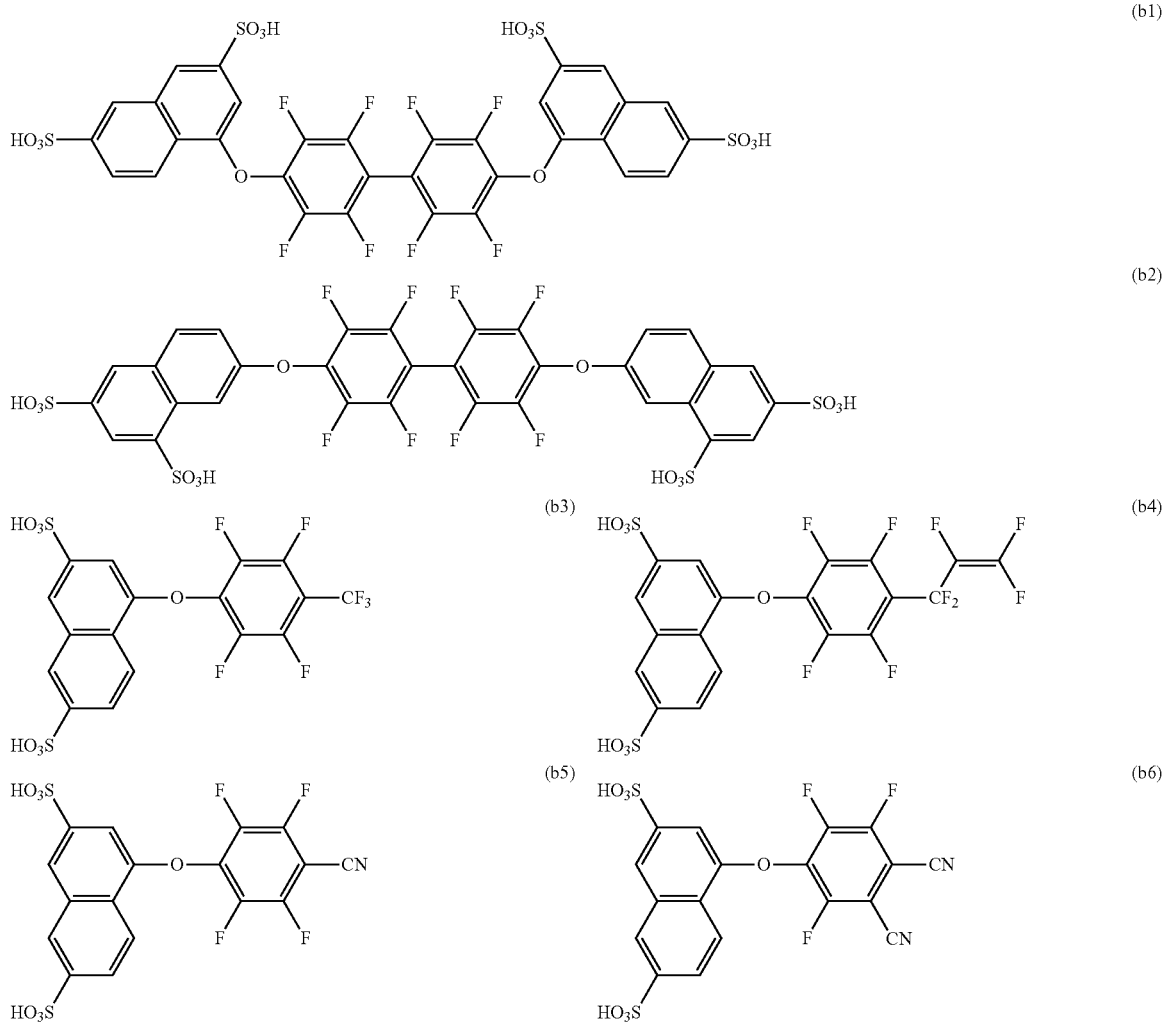

In cases where a dopant substance is included in the charge-transporting varnish of the invention, the amount in which to use the dopant substance is determined as appropriate based on such considerations as the type of dopant substance and the desired degree of charge transportability and thus cannot be strictly specified. However, expressed in terms of a weight ratio, this is generally included in a weight ratio relative to unity (1) for the charge-transporting substance consisting of the inventive triphenylamine derivative (referred to below as simply the "charge-transporting substance") of from about 0.01 to about 50.

Notably, in cases where a heteropolyacid is used as the dopant substance, by setting the heteropolyacid to a weight ratio relative to unity (1) for the charge-transporting substance of from about 0.5 to about 30.0, preferably from about 1.0 to about 20.0, more preferably from about 2.0 to about 15.0, even more preferably from about 3.0 to about 12.0, and still more preferably from about 4.0 to about 11.0, a charge-transporting thin-film that imparts a high brightness when used in organic EL devices can be reproducibly obtained. That is, in such charge-transporting varnishes, the ratio of the weight of heteropolyacid ($W_D$) to the weight of charge-transporting substance ($W_H$) satisfies the relationship $0.5 \leq W_D/W_H \leq 30.0$, preferably satisfies the relationship $1.0 \leq W_D/W_H \leq 20.0$, more preferably satisfies the relationship $2.0 \leq W_D/W_H \leq 15.0$, even more preferably satisfies the relationship $3.0 \leq W_D/W_H \leq 12.0$, and even still more preferably satisfies the relationship $4.0 \leq W_D/W_H \leq 11.0$.

On the other hand, in cases where an arylsulfonic acid compound is used as the dopant substance, by setting the arylsulfonic acid compound to a molar ratio relative to unity (1) for the charge-transporting substance of from 0.05 to 15.0, preferably from 0.10 to 10.0, more preferably from 0.25 to 7.0, even more preferably from 0.50 to 5.0, and still more preferably from 0.75 to 3.0, a charge-transporting thin-film that imparts a high brightness when used in organic EL devices can be reproducibly obtained. That is, in such charge-transporting varnishes, the ratio of the mole number of arylsulfonic acid compound ($M_A$) to the mole number of charge-transporting substance ($M_H$) satisfies the relationship $0.05 \leq M_A/M_H \leq 15.0$, preferably satisfies the relationship $0.1 \leq M_A/M_H \leq 10.0$, more preferably satisfies the relationship $0.25 \leq M_A/M_H \leq 7.0$, even more preferably satisfies the relationship $0.50 \leq M_A/M_H \leq 5.0$, and still more preferably satisfies the relationship $0.75 \leq M_A/M_H \leq 3.0$.

In addition, the charge-transporting varnish of the invention may include an organosilane compound. By including an organosilane compound, the ability to inject holes into a layer that is stacked so as to be in contact with the hole injection layer on the side opposite from the positive electrode—be it a hole transport layer or an emissive layer—can be increased, as a result of which even higher brightness characteristics can be achieved.

This organosilane compound is exemplified by dialkoxysilane compounds, trialkoxysilane compounds and tetraalkoxysilane compounds. These may be used singly, or two or more may be used in combination.

In particular, the organosilane compound is preferably a dialkoxysilane compound or a trialkoxysilane compound, and more preferably a trialkoxysilane compound.

The tetraalkoxysilane compounds, trialkoxysilane compounds and dialkoxysilane compounds are exemplified by compounds of formulas (8) to (10).

$$Si(OR)_4 \tag{8}$$

$$SiR'(OR)_3 \tag{9}$$

$$Si(R')_2(OR)_2 \tag{10}$$

In these formulas, each R is independently an alkyl group of 1 to 20 carbons which may be substituted with $Z^4$, an alkenyl group of 2 to 20 carbons which may be substituted with $Z^4$, an alkynyl group of 2 to 20 carbons which may be substituted with $Z^4$, an aryl group of 6 to 20 carbons which may be substituted with $Z^5$, or a heteroaryl group of 2 to 20 carbons which may be substituted with $Z^5$. Each R' is independently an alkyl group of 1 to 20 carbons which may be substituted with $Z^6$, an alkenyl group of 2 to 20 carbons which may be substituted with $Z^6$, an alkynyl group of 2 to 20 carbons which may be substituted with $Z^6$, an aryl group of 6 to 20 carbons which may be substituted with $Z^7$, or a heteroaryl group of 2 to 20 carbons which may be substituted with $Z^7$.

$Z^4$ is a halogen atom, an aryl group of 6 to 20 carbons which may be substituted with $Z^8$, or a heteroaryl group of 2 to 20 carbons which may be substituted with $Z^8$. $Z^5$ is a halogen atom, an alkyl group of 1 to 20 carbons which may be substituted with $Z^8$, an alkenyl group of 2 to 20 carbons which may be substituted with $Z^8$, or an alkynyl group of 2 to 20 carbons which may be substituted with $Z^8$.

$Z^6$ is a halogen atom, an aryl group of 6 to 20 carbons which may be substituted with $Z^8$, a heteroaryl group of 2 to 20 carbons which may be substituted with $Z^8$, an epoxycyclohexyl group, a glycidoxy group, a methacryloxy group, an acryloxy group, a ureido group (—NHCONH$_2$), a thiol group, an isocyanate group (—NCO), an amino group, the group —NHY$^{14}$ or the group —NY$^{15}$Y$^{16}$. $Z^7$ a halogen atom, an alkyl group of 1 to 20 carbons which may be substituted with $Z^8$, an alkenyl group of 2 to 20 carbons which may be substituted with $Z^8$, an alkynyl group of 2 to 20 carbons which may be substituted with $Z^8$, an epoxycyclohexyl group, a glycidoxy group, a methacryloxy group, an acryloxy group, a ureido group (—NHCONH$_2$), a thiol group, an isocyanate group (—NCO), an amino group, the group —NHY$^{14}$ or the group —NY$^{15}$Y$^{16}$. Y$^{14}$ to Y$^{16}$ are each independently an alkyl group of 1 to 20 carbons which may be substituted with $Z^8$, an alkenyl group of 2 to 20 carbons which may be substituted with $Z^8$, an alkynyl group of 2 to 20 carbons which may be substituted with $Z^8$, an aryl group of 6 to 20 carbons which may be substituted with $Z^8$, or a heteroaryl group of 2 to 20 carbons which may be substituted with $Z^8$.

$Z^8$ is a halogen atom, an amino group, a nitro group, a cyano group or a thiol group.

In formulas (8) to (10), the halogen atom, alkyl group of 1 to 20 carbons, alkenyl group of 2 to 20 carbons, alkynyl group of 2 to 20 carbons, aryl group of 6 to 20 carbons and heteroaryl group of 2 to 20 carbons are exemplified in the same way as above.

In R and R', the number of carbons on the alkyl, alkenyl and alkynyl groups is preferably not more than 10, more preferably not more than 6, and even more preferably not more than 4.

Also, the number of carbons on the aryl and heteroaryl groups is preferably not more than 14, more preferably not more than 10, and even more preferably not more than 6.

R is preferably an alkyl group of 1 to 20 carbons or an alkenyl group of 2 to 20 carbons which may be substituted with $Z^4$, or an aryl group of 6 to 20 carbons which may be substituted with $Z^5$; more preferably an alkyl group of 1 to 6 carbons or an alkenyl group of 2 to 6 carbons which may be substituted with $Z^4$, or a phenyl group which may be substituted with $Z^5$; even more preferably an alkyl group of 1 to 4 carbons which may be substituted with $Z^4$ or a phenyl group which may be substituted with $Z^5$; and still more preferably a methyl group or ethyl group which may be substituted with $Z^4$.

R' is preferably an alkyl group of 1 to 20 carbons which may be substituted with $Z^6$, or an aryl group of 6 to 20 carbons which may be substituted with $Z^7$; more preferably an alkyl group of 1 to 10 carbons which may be substituted with $Z^6$, or an aryl group of 6 to 14 carbons which may be substituted with $Z^7$; even more preferably an alkyl group of 1 to 6 carbons which may be substituted with $Z^6$, or an aryl group of 6 to 10 carbons which may be substituted with $Z^7$; and still more preferably an alkyl group of 1 to 4 carbons which may be substituted with $Z^6$, or a phenyl group which may be substituted with $Z^7$.

The plurality of R moieties may all be the same or different, and the plurality of R' moieties may likewise all be the same or different.

$Z^4$ is preferably a halogen atom, or an aryl group of 6 to 20 carbons which may be substituted with $Z^8$; more preferably a fluorine atom or a phenyl group which may be substituted with $Z^8$; and most preferably does not exist (i.e., is non-substituting).

$Z^5$ is preferably a halogen atom, or an alkyl group of 6 to 20 carbons which may be substituted with $Z^8$; more preferably a fluorine atom, or an alkyl of 1 to 10 carbons which may be substituted with $Z^8$; and most preferably does not exist (i.e., is non-substituting).

$Z^6$ is preferably a halogen atom, a phenyl group which may be substituted with $Z^8$, a furanyl group which may be substituted with $Z^8$, an epoxycyclohexyl group, a glycidoxy group, a methacryloxy group, an acryloxy group, a ureido group, a thiol group, an isocyanate group, an amino group, a phenylamino group which may be substituted with $Z^8$, or a diphenylamino group which may be substituted with $Z^8$; more preferably a halogen atom; and even more preferably a fluorine atom or does not exist (i.e., is non-substituting).

$Z^7$ is preferably a halogen atom, an alkyl group of 1 to 20 carbons which may be substituted with $Z^8$, a furanyl group which may be substituted with $Z^8$, an epoxycyclohexyl group, a glycidoxy group, a methacryloxy group, an acryloxy group, a ureido group, a thiol group, an isocyanate group, an amino group, a phenylamino group which may be substituted with $Z^8$, or a diphenylamino group which may be substituted with $Z^8$; more preferably a halogen atom; and even more preferably a fluorine atom or does not exist (i.e., is non-substituting).

$Z^8$ is preferably a halogen atom, and more preferably a fluorine atom or does not exist (i.e., is non-substituting).

Examples of organosilane compounds that may be used in this invention include, but are not limited to, the following.

Examples of dialkoxysilane compounds include dimethyldimethoxysilane, dimethyldiethoxysilane, methylethyldimethoxysilane, diethyldimethoxysilane, diethyldiethoxysilane, methylpropyldimethoxysilane, methylpropyldiethoxysilane, diisopropyldimethoxysilane, phenylmethyldimethoxysilane, vinylmethyldimethoxysilane, 3-glycidoxypropylmethyldimethoxysilane, 3-glycidoxypropylmethyldiethoxysilane, 3-(3,4-epoxycyclohexyl)ethylmethyldimethoxysilane, 3-methacryloxypropylmethyldimethoxysilane, 3-methacryloxypropylmethyldiethoxysilane, 3-mercaptopropylmethyldimethoxysilane, γ-aminopropylmethyldiethoxysilane, N-(2-aminoethyl)aminopropylmethyldimethoxysilane and 3,3,3-trifluoropropylmethyldimethoxysilane.

Examples of trialkoxysilane compounds include methyltrimethoxysilane, methyltriethoxysilane, ethyltrimethoxysilane, ethyltriethoxysilane, propyltrimethoxysilane, propyltriethoxysilane, butyltrimethoxysilane, butyltriethoxysilane, pentyltrimethoxysilane, pentyltriethoxysilane, heptyltrimethoxysilane, heptyltriethoxysilane, octyltrimethoxysilane, octyltriethoxysilane, dodecyltrimethoxysilane, dodecyltriethoxysilane, hexadecyltrimethoxysilane, hexadecyltriethoxysilane, octadecyltrimethoxysilane, octadecyltriethoxysilane, phenyltrimethoxysilane, phenyltriethoxysilane, vinyltrimethoxysilane, vinyltriethoxysilane, γ-aminopropyltrimethoxysilane, 3-aminopropyltriethoxysilane, γ-glycidoxypropyltrimethoxysilane, 3-glycidoxypropyltriethoxysilane, γ-methacryloxypropyltrimethoxysilane, γ-methacryloxypropyltriethoxysilane, triethoxy(4-(trifluoromethyl)phenyl)silane, dodecyltriethoxysilane, 3,3,3-trifluoropropyltrimethoxysilane, (triethoxysilyl)cyclohexane, perfluorooctylethyltriethoxysilane, triethoxyfluorosilane, tridecafluoro-1,1,2,2,-tetrahydrooctyltriethoxysilane, pentafluorophenyltrimethoxysilane, pentafluorophenyltriethoxysilane, 3-(heptafluoroisopropoxy)propyltriethoxysilane, heptadecafluoro-1,1,2,2-tetrahydrodecyltriethoxysilane, triethoxy-2-thienylsilane and 3-(triethoxysilyl)furan.

Examples of tetraalkoxysilane compounds include tetraethoxysilane, tetramethoxysilane and tetrapropoxysilane.

Of these, 3,3,3-trifluoropropylmethyldimethoxysilane, triethoxy(4-(trifluoromethyl)phenyl)silane, 3,3,3-trifluoropropyltrimethoxysilane, perfluorooctylethyltriethoxysilane, pentafluorophenyltrimethoxysilane and pentafluorophenyltriethoxysilane are preferred.

In cases where an organosilane compound is included in the charge-transporting varnish of the invention, from the standpoint of maintaining the high charge transportability of the thin-film obtained therefrom, the content of the organosilane compound, with respect to the total weight of the charge-transporting substance and the dopant substance, is generally from about 0.1 to about 50 weight %. However, to suppress a decrease in the charge transportability of the resulting thin-film and to increase the ability to inject holes in a layer that is stacked so as to be in contact with the hole injection layer on the side opposite from the positive electrode—be it a hole transport layer or an emissive layer, the content is preferably from about 0.5 to about 40 weight %, more preferably from about 0.8 to about 30 weight %, and even more preferably from about 1 to about 20 weight %.

In addition to a charge-transporting substance consisting of the above-described triphenylamine derivative, the charge-transporting varnish of the invention may include also a known charge-transporting substance.

Highly solvating solvents which are able to dissolve well the charge-transporting substance and the dopant substance may be used as the organic solvent employed when preparing the charge-transporting varnish.

Examples of such highly solvating solvents that may be used include organic solvents such as N,N-dimethylformamide, N,N-dimethylacetamide, N-methylpyrrolidone, 1,3-dimethyl-2-imidazolidinone and diethylene glycol monomethyl ether. These solvents may be used singly, or two or more may be used in admixture. The amount of use thereof may be set to from 5 to 100 weight %, based on the overall solvent used in the varnish.

The charge-transporting substance and dopant substance are preferably in a state where both are either completely dissolved or uniformly dispersed in the solvent; and are more preferably completely dissolved.

In this invention, by including in the varnish at least one high-viscosity organic solvent having a viscosity at 25° C. of from 10 to 200 mPa·s, and especially from 35 to 150 mPa·s, and a boiling point at standard pressure (atmospheric pressure) of from 50 to 300° C., and especially from 150 to 250° C., the viscosity of the varnish is easy to adjust, as a result of which the preparation of a varnish that reproducibly gives thin-films of high flatness and accords with the coating method to be used is possible.

Examples of the high-viscosity organic solvent include, but are not particularly limited to, cyclohexanol, ethylene glycol, ethylene glycol diglycidyl ether, 1,3-octylene glycol, diethylene glycol, dipropylene glycol, triethylene glycol, tripropylene glycol, 1,3-butanediol, 2,3-butanediol, 1,4-butanediol, propylene glycol and hexylene glycol. These solvents may be used singly, or two or more may be used in admixture.

The amount of high-viscosity organic solvent added as a proportion of the overall solvent used in the varnish of the invention is preferably within a range where no precipitation of solids occurs. To the extent that solids do not precipitate, the amount of such addition is preferably from 5 to 80 weight %.

In addition, other solvents may be admixed in a proportion with respect to the overall solvent used in the varnish of from 1 to 90 weight %, and preferably from 1 to 50 weight %, for such purposes as to enhance the substrate wettability by the varnish, adjust the solvent surface tension, adjust the polarity and adjust the boiling point.

Examples of such solvents include, but are not limited to, propylene glycol monomethyl ether, ethylene glycol monobutyl ether, diethylene glycol diethyl ether, diethylene glycol dimethyl ether, diethylene glycol monoethyl ether acetate, diethylene glycol monobutyl ether acetate, dipropylene glycol monomethyl ether, propylene glycol monomethyl ether acetate, diethylene glycol monoethyl ether, diacetone alcohol, γ-butyrolactone, ethyl lactate and n-hexyl acetate. These solvents may be used singly, or two or more may be used in admixture.

The viscosity of the inventive varnish is set as appropriate for such considerations as the thickness of the thin-film to be produced and the solids concentration of the varnish, but is generally from 1 to 50 mPa·s at 25° C.

The solids concentration of the charge-transporting varnish of this invention is set as appropriate based on such considerations as the viscosity, surface tension and other properties of the varnish and the thickness and other properties of the thin-film to be produced, and is generally from about 0.1 to about 10.0 weight %. From the standpoint of improving the coating properties of the varnish, the solids concentration of the varnish is preferably from 0.5 to 5.0 weight %, and more preferably from 1.0 to 3.0 weight %.

By coating the charge-transporting varnish of the invention onto a substrate and baking, a charge-transporting thin-film can be formed on the substrate.

Examples of the varnish coating method include, but are not particularly limited to, dipping, spin coating, transfer printing, roll coating, brush coating, inkjet printing and spraying. It is preferable to adjust the viscosity and surface tension of the varnish according to the coating method to be used.

When using the varnish of the invention, the baking atmosphere is not particularly limited. A thin-film having a uniform film surface and high charge transportability can be obtained not only in an open-air atmosphere, but even in an inert gas such as nitrogen or in a vacuum.

The baking temperature is suitably set in a range of generally from about 100 to about 260° C. while taking into consideration such factors as the intended use of the resulting thin-film and the degree of charge transportability to be imparted to the resulting thin-film. In cases where the resulting thin-film is to be used as a hole injection layer in an organic EL device, the baking temperature is preferably from about 140 to about 250° C., and more preferably from about 145 to about 240° C.

During baking, a temperature change in two or more steps may be applied for such purposes as to manifest a more uniform film formability or to induce the reaction to proceed on the substrate. Heating may be carried out using a suitable apparatus such as a hot plate or an oven.

Although the thickness of the charge-transporting thin-film is not particularly limited, when the thin-film is to be used as a hole injection layer in an organic EL device, a film thickness of from 5 to 200 nm is preferred. Methods of varying the film thickness include, for example, varying the solids concentration in the varnish and varying the amount of solution on the substrate during coating.

Examples of the materials and method used to fabricate organic light-emitting diode (OLED) devices using the charge-transporting varnish of the invention include, but are not limited to, those mentioned below.

The electrode substrate to be used is preferably cleaned by carrying out liquid washing beforehand with a cleaning agent, alcohol, pure water or the like. For example, in the case of a positive electrode substrate, it is preferable to carry out surface treatment such as UV/ozone treatment or oxygen-plasma treatment just prior to use. However, when the positive electrode material is composed primarily of organic substances, surface treatment need not be carried out.

An example of a method of manufacturing an OLED device having a hole injection layer composed of a thin-film obtained from the charge-transporting varnish of the invention is described below.

Using the above methods, a hole injection layer is formed on an electrode by coating the charge-transporting varnish of the invention onto a positive electrode substrate and baking. The workpiece is then introduced into a vacuum deposition system, where a hole transport layer, emissive layer, electron transport layer, electron transport layer/hole-blocking layer and negative electrode metal are vapor-deposited in this order to form the OLED device. Where necessary, an electron-blocking layer may be provided between the emissive layer and the hole transport layer.

Illustrative examples of positive electrode materials include transparent electrodes such as indium-tin oxide (ITO) and indium-zinc oxide (IZO), and metal positive electrodes made of a metal such as aluminum or of an alloy of such a metal. A positive electrode material on which planarizing treatment has been carried out is preferred. Use can also be made of polythiophene derivatives and polyaniline derivatives having high charge transportability.

Examples of other metals making up the metal positive electrode include, but are not limited to, scandium, titanium, vanadium, chromium, manganese, iron, cobalt, nickel, copper, zinc, gallium, yttrium, zirconium, niobium, molybdenum, ruthenium, rhodium, palladium, cadmium, indium, scandium, lanthanum, cerium, praseodymium, neodymium, promethium, samarium, europium, gadolinium, terbium, dysprosium, holmium, erbium, thulium, ytterbium, hafnium, thallium, tungsten, rhenium, osmium, iridium, platinum, gold, titanium, lead, bismuth, and alloys thereof.

Illustrative examples of hole transport layer-forming materials include triarylamines such as
(triphenylamine)dimer derivatives,
[(triphenylamine)dimer]spirodimer,
N,N'-bis(naphthalen-1-yl)-N,N'-bis(phenyl)benzidine (α-NPD),
N,N'-bis(naphthalene-2-yl)-N,N'-bis(phenyl)benzidine,
N,N'-bis(3-methylphenyl)-N,N'-bis(phenyl)benzidine,
N,N'-bis(3-methylphenyl)-N,N'-bis(phenyl)-9,9-spirobifluorene,
N,N'-bis(naphthalen-1-yl)-N,N'-bis(phenyl)-9,9-spirobifluorene,
N,N'-bis(3-methylphenyl)-N,N'-bis(phenyl)-9,9-dimethylfluorene,
N,N'-bis(naphthalen-1-yl)-N,N'-bis(phenyl)-9,9-dimethylfluorene,
N,N'-bis(3-methylphenyl)-N,N'-bis(phenyl)-9,9-diphenylfluorene,
N,N'-bis(naphthalen-1-yl)-N,N'-bis(phenyl)-9,9-diphenylfluorene,
N,N'-bis(naphthalen-1-yl)-N,N'-bis(phenyl)-2,2'-dimethylbenzidine,
2,2',7,7'-tetrakis(N,N-diphenylamino)-9,9-spirobifluorene,
9,9-bis[4-(N,N-bisbiphenyl-4-ylamino)phenyl]-9H-fluorene,
9,9-bis[4-(N,N-bisnaphthalen-2-ylamino)phenyl]-9H-fluorene,
9,9-bis[4-(N-naphthalen-1-yl-N-phenylamino)phenyl]-9H-fluorene,
2,2',7,7'-tetrakis[N-naphthalenyl(phenyl)amino]-9,9-spirobifluorene,
N,N'-bis(phenanthren-9-yl)-N,N'-bis(phenyl)benzidine,
2,2'-bis[N,N-bis(biphenyl-4-yl)amino]-9,9-spirobifluorene,
2,2'-bis(N,N-diphenylamino)-9,9-spirobifluorene,
di[4-(N,N-di(p-tolyl)amino)phenyl]cyclohexane,
2,2',7,7'-tetra(N,N-di(p-tolyl))amino-9,9-spirobifluorene,
N,N,N',N'-tetranaphthalen-2-ylbenzidine,
N,N,N',N'-tetra(3-methylphenyl)-3,3'-dimethylbenzidine,
N,N'-di(naphthalenyl)-N,N'-di(naphthalen-2-yl)benzidine,
N,N,N',N'-tetra(naphthalenyl)benzidine,
N,N'-di(naphthalen-2-yl)-N,N'-diphenylbenzidine-1-4-diamine,
$N^1,N^4$-diphenyl-$N^1,N^4$-di(m-tolyl)benzene-1,4-diamine,
$N^2,N^2,N^6,N^6$-tetraphenylnaphthalene-2,6-diamine,
tris(4-(quinolin-8-yl)phenyl)amine,
2,2'-bis(3-(N,N-di(p-tolyl)amino)phenyl)biphenyl,
4,4',4''-tris[3-methylphenyl(phenyl)amino]triphenylamine (m-MTDATA) and
4,4',4''-tris[1-naphthyl(phenyl)amino]triphenylamine (1-TNATA);
and oligothiophenes such as
5,5''-bis-{4-[bis(4-methylphenyl)amino]phenyl}-2,2':5',2''-terthiophene (BMA-3T).

Illustrative examples of emissive layer-forming materials include tris(8-quinolinolate)aluminum(III) (Alq$_3$), bis(8-quinolinolate) zinc(II) (Znq$_2$), bis(2-methyl-8-quinolinolate)(p-phenylphenolate)aluminum(III) (BAlq),
4,4'-bis(2,2-diphenylvinyl)biphenyl,
9,10-di(naphthalen-2-yl)anthracene,
2-t-butyl-9,10-di(naphthalen-2-yl)anthracene,
2,7-bis[9,9-di(4-methylphenyl)fluoren-2-yl]-9,9-di(4-methyl-phenyl)fluorene,
2-methyl-9,10-bis(naphthalen-2-yl)anthracene,
2-(9,9-spirobifluoren-2-yl)-9,9-spirobifluorene,
2,7-bis(9,9-spirobifluoren-2-yl)-9,9-spirobifluorene,
2-[9,9-di(4-methylphenyl)fluoren-2-yl]-9,9-di(4-methylphenyl)fluorene,
2,2'-dipyrenyl-9,9-spirobifluorene,
1,3,5-tris(pyren-1-yl)benzene,
9,9-bis[4-(pyrenyl)phenyl]-9H-fluorene,
2,2'-bi(9,10-diphenylanthracene),
2,7-dipyrenyl-9,9-spirobifluorene, 1,4-di(pyren-1-yl)benzene,
1,3-di(pyren-1-yl)benzene, 6,13-di(biphenyl-4-yl)pentacene,
3,9-di(naphthalen-2-yl)perylene,
3,10-di(naphthalen-2-yl)perylene,
tris[4-(pyrenyl)phenyl]amine,
10,10'-di(biphenyl-4-yl)-9,9'-bianthracene,
N,N'-di(naphthalen-1-yl)-N,N'-diphenyl[1,1':4',1":4",1'''-quaterphenyl]-4,4'''-diamine,
4,4'-di[10-(naphthalen-1-yl)anthracen-9-yl]biphenyl,
dibenzo{[f,f']-4,4',7,7'-tetraphenyl}diindeno[1,2,3-cd:1',2',3'-lm]perylene,
1-(7-(9,9'-bianthracen-10-yl)-9,9-dimethyl-9H-fluoren-2-yl)pyrene,
1-(7-(9,9'-bianthracen-10-yl)-9,9-dihexyl-9H-fluoren-2-yl)pyrene,
1,3-bis(carbazol-9-yl)benzene,
1,3,5-tris(carbazol-9-yl)benzene,
4,4',4"-tris(carbazol-9-yl)triphenylamine,
4,4'-bis(carbazol-9-yl)biphenyl,
4,4'-bis(carbazol-9-yl)-2,2'-dimethylbiphenyl,
2,7-bis(carbazol-9-yl)-9,9-dimethylfluorene,
2,2',7,7'-tetrakis(carbazol-9-yl)-9,9-spirobifluorene,
2,7-bis(carbazol-9-yl)-9,9-di(p-tolyl)fluorene,
9,9-bis[4-(carbazol-9-yl)phenyl]fluorene,
2,7-bis(carbazol-9-yl)-9,9-spirobifluorene,
1,4-bis(triphenylsilyl)benzene, 1,3-bis(triphenylsilyl)benzene,
bis(4-N,N-diethylamino-2-methylphenyl)-4-methylphenylmethane,
2,7-bis(carbazol-9-yl)-9,9-dioctylfluorene,
4,4"-di(triphenylsilyl)-p-terphenyl,
4,4'-di(triphenylsilyl)biphenyl,
9-(4-t-butylphenyl)-3,6-bis(triphenylsilyl)-9H-carbazole,
9-(4-t-butylphenyl)-3,6-ditrityl-9H-carbazole,
9-(4-t-butylphenyl)-3,6-bis(9-(4-methoxyphenyl)-9H-fluoren-9-yl)-9H-carbazole,
2,6-bis(3-(9H-carbazol-9-yl)phenyl)pyridine,
triphenyl(4-(9-phenyl-9H-fluoren-9-yl)phenyl)silane,
9,9-dimethyl-N,N-diphenyl-7-(4-(1-phenyl-1H-benzo[d]imidazol-2-yl)phenyl-9H-fluoren-2-amine,
3,5-bis(3-(9H-carbazol-9-yl)phenyl)pyridine,
9,9-spirobifluoren-2-yldiphenylphosphine oxide,
9,9'-(5-triphenylsilyl)-1,3-phenylene)bis(9H-carbazole),
3-(2,7-bis(diphenylphosphoryl)-9-phenyl-9H-fluoren-9-yl)-9-phenyl-9H-carbazole,
4,4,8,8,12,12-hexa(p-tolyl)-4H-8H-12H-12C-azadibenzo[cd,mn]-pyrene,
4,7-di(9H-carbazol-9-yl)-1,10-phenanthroline,
2,2'-bis(4-(carbazol-9-yl)phenyl)biphenyl,
2,8-bis(diphenylphosphoryl)dibenzo[b,d]thiophene,
bis(2-methylphenyl)diphenylsilane,
bis[3,5-di(9H-carbazol-9-yl)phenyl]diphenylsilane,
3,6-bis(carbazol-9-yl)-9-(2-ethylhexyl)-9H-carbazole,
3-(diphenylphosphoryl)-9-(4-(diphenylphosphoryl)phenyl)-9H-carbazole and
3,6-bis[(3,5-diphenyl)phenyl]-9-phenylcarbazole.

It is also possible to form the emissive layer by the co-vapor deposition of any of these materials with a light-emitting dopant.

Illustrative examples of light-emitting dopants include 3-(2-benzothiazolyl)-7-(diethylamino)coumarin,
2,3,6,7-tetrahydro-1,1,7,7-tetramethyl-1H,5H,11H-10-(2-benzothiazolyl)quinolidino[9,9a,1gh]coumarin,
quinacridone, N,N'-dimethylquinacridone,
tris(2-phenylpyridine) iridium(III) (Ir(ppy)$_3$),
bis(2-phenylpyridine)(acetylacetonate) iridium(III) (Ir(ppy)$_2$(acac)),
tris[2-(p-tolyl)pyridine) iridium(III) (Ir(mppy)$_3$),
9,10-bis[N,N-di(p-tolyl)amino]anthracene,
9,10-bis[phenyl(m-tolyl)amino]anthracene,
bis[2-(2-hydroxyphenyl)benzothiazolate]zinc(II),
$N^{10},N^{10},N^{10'},N^{10'}$-tetra(p-tolyl)-9,9'-bianthracene-10,10'-diamine,
$N^{10},N^{10},N^{10'},N^{10'}$-tetraphenyl-9,9'-bianthracene-10,10'-diamine,
$N^{10},N^{10'}$-diphenyl-$N^{10},N^{10'}$-dinaphthalenyl-9,9'-bianthracene-10,10'-diamine,
4,4'-bis(9-ethyl-3-carbazovinylene)-1,1'-biphenyl, perylene, 2,5,8,11-tetra-t-butylperylene,
1,4-bis[2-(3-N-ethylcarbazolyl)vinyl]benzene,
4,4'-bis[4-(di-p-tolylamino)styryl]biphenyl,
4-(di-p-tolylamino)-4'-[(di-p-tolylamino)styryl]stilbene,
bis[3,5-difluoro-2-(2-pyridyl)phenyl-(2-carboxypyridyl)] iridium(III),
4,4'-bis[4-(diphenylamino)styryl]biphenyl,
bis(2,4-difluorophenylpyridinato)tetrakis(1-pyrazolyl)borate iridium(III),
N,N'-bis(naphthalen-2-yl)-N,N'-bis(phenyl)tris(9,9-dimethylfluorenylene),
2,7-bis{2-[phenyl(m-tolyl)amino]-9,9-dimethylfluoren-7-yl}-9,9-dimethylfluorene,
N-(4-((E)-2-(6((E)-4-(diphenylamino)styryl)naphthalen-2-yl)-vinyl)phenyl)-N-phenylbenzenamine,
fac-iridium(III) tris(1-phenyl-3-methylbenzimidazolin-2-ylidene-C,C$^{2'}$),
mer-iridium(III) tris(1-phenyl-3-methylbenzimidazolin-2-ylidene-C,C$^{2'}$),
2,7-bis[4-(diphenylamino)styryl]-9,9-spirobifluorene,
6-methyl-2-(4-(9-(4-(6-methylbenzo[d]thiazol-2-yl)phenyl)-anthracen-10-yl)phenyl)benzo[d]thiazole,
1,4-di[4-(N,N-diphenyl)amino]styrylbenzene,
1,4-bis(4-(9H-carbazol-9-yl)styryl)benzene,
(E)-6-(4-(diphenylamino)styryl)-N,N-diphenylnaphthalen-2-amine,
bis(2,4-difluorophenylpyridinato)(5-(pyridin-2-yl)-1H-tetrazolate) iridium(III),
bis(3-trifluoromethyl-5-(2-pyridyl)pyrazole)((2,4-difluorobenzyl)diphenylphosphinate) iridium(III),
bis(3-trifluoromethyl-5-(2-pyridyl)pyrazolate)(benzyl-diphenylphosphinate) iridium(III), bis(1-(2,4-difluorobenzyl)-3-methylbenzimidazolium)(3-(trifluoromethyl)-5-(2-pyridyl)-1,2,4-triazolate) iridium (III),
bis(3-trifluoromethyl-5-(2-pyridyl)pyrazolate)(4',6'-difluorophenylpyridinate) iridium(III),
bis(4',6'-difluorophenylpyridinato)(3,5-bis(trifluoromethyl)-2-(2'-pyridyl)pyrrolate) iridium(III),
bis(4',6'-difluorophenylpyridinato)(3-(trifluoromethyl)-5-(2-pyridyl)-1,2,4-triazolate) iridium (III),
(Z)-6-mesityl-N-(6-mesitylquinolin-2(1H)-ylidene)quinoline-2-amine-$BF_2$,
(E)-2-(2-(4-(dimethylamino)styryl)-6-methyl-4H-pyran-4-ylidene)malononitrile,
4-(dicyanomethylene)-2-methyl-6-julolidyl-9-enyl-4-H-pyran,
4-(dicyanomethylene)-2-methyl-6-(1,1,7,7-tetramethyljulolidyl-9-enyl)-4H-pyran,
4-(dicyanomethylene)-2-t-butyl-6-(1,1,7,7-tetramethyljulolidin-4-ylvinyl)-4H-pyran,
tris(dibenzoylmethane)phenanthroline europium(III),
5,6,11,12-tetraphenylnaphthacene,
bis(2-benzo[b]thiophen-2-yl-pyridin)(acetylacetonate) iridium(III),
tris(1-phenylisoquinoline) iridium(III),
bis(1-phenylisoquinoline)(acetylacetonate) iridium(III),
bis[1-(9,9-dimethyl-9H-fluoren-2-yl)isoquinoline]-(acetylacetonate) iridium(III),
bis[2-(9,9-dimethyl-9H-fluoren-2-yl)quinoline]-(acetylacetonate) iridium(III),
tris[4,4'-di-t-butyl-(2,2')-bipyridine]ruthenium(III).bis(hexafluorophosphate),
tris(2-phenylquinoline) iridium(III),
bis(2-phenylquinoline)(acetylacetonate) iridium(III),
2,8-di-t-butyl-5,11-bis(4-t-butylphenyl)-6,12-diphenyltetracene,
bis(2-phenylbenzothiazolate)(acetylacetonate) iridium(III),
platinum 5,10,15,20-tetraphenyltetrabenzoporphyrin,
osmium(II) bis(3-trifluoromethyl-5-(2-pyridine)pyrazolate)-dimethylphenylphosphine,
osmium(II) bis(3-trifluoromethyl)-5-(4-t-butylpyridyl)-1,2,4-triazolate)diphenylmethylphosphine,
osmium(II) bis(3-(trifluoromethyl)-5-(2-pyridyl)-1,2,4-triazole)dimethylphenylphosphine,
osmium(II) bis(3-(trifluoromethyl)-5-(4-t-butylpyridyl)-1,2,4-triazolate)dimethylphenylphosphine,
bis[2-(4-n-hexylphenyl)quinoline](acetylacetonate) iridium (III),
tris[2-(4-n-hexylphenyl)quinoline]iridium(III),
tris[2-phenyl-4-methylquinoline]iridium(III),
bis(2-phenylquinoline)(2-(3-methylphenyl)pyridinate) iridium(III),
bis(2-(9,9-diethylfluoren-2-yl)-1-phenyl-1H-benzo[d]-imidazolato)(acetylacetonate) iridium(III),
bis(2-phenylpyridine)(3-(pyridin-2-yl)-2H-chromen-9-onate) iridium(III),
bis(2-phenylquinoline)(2,2,6,6-tetramethylheptane-3,5-dionate) iridium(III),
bis(phenylisoquinoline)(2,2,6,6-tetramethylheptane-3,5-dionate) iridium(III),
iridium(III) bis(4-phenylthieno[3,2-c]pyridinato-N,$C^{2'}$) acetylacetonate,
(E)-2-(2-t-butyl-6-(2-(2,6,6-trimethyl-2,4,5,6-tetrahydro-1H-pyrrolo[3,2,1-ij]quinolin-8-yl)vinyl)-4H-pyran-4-ylidene)-malononitrile,
bis(3-trifluoromethyl-5-(1-isoquinolyl)pyrazolate)(methyldiphenylphosphine) ruthenium,
bis[(4-n-hexylphenyl)isoquinoline](acetylacetonate) iridium(III),
platinum(II) octaethylporphin,
bis(2-methyldibenzo[f,h]quinoxaline)(acetylacetonate) iridium(III) and
tris[(4-n-hexylphenyl)isoquinoline]iridium(III).

Illustrative examples of electron transport layer/hole-blocking layer-forming materials include
lithium 8-hydroxyquinolinate,
2,2',2"-(1,3,5-benzinetriyl)-tris(1-phenyl-1-H-benzimidazole),
2-(4-biphenyl)-5-(4-t-butylphenyl)-1,3,4-oxadiazole,
2,9-dimethyl-4,7-diphenyl-1,10-phenanthroline,
4,7-diphenyl-1,10-phenanthroline,
bis(2-methyl-8-quinolinolate)-4-(phenylphenolato)aluminum,
1,3-bis[2-(2,2'-bipyridin-6-yl)-1,3,4-oxadiazo-5-yl]benzene,
6,6'-bis[5-(biphenyl-4-yl)-1,3,4-oxadiazo-2-yl]-2,2'-bipyridine,
3-(4-biphenyl)-4-phenyl-5-t-butylphenyl-1,2,4-triazole,
4-(naphthalen-1-yl)-3,5-diphenyl-4H-1,2,4-triazole,
2,9-bis(naphthalen-2-yl)-4,7-diphenyl-1,10-phenanthroline,
2,7-bis[2-(2,2'-bipyridin-6-yl)-1,3,4-oxadiazo-5-yl]-9,9-dimethylfluorene,
1,3-bis[2-(4-t-butylphenyl)-1,3,4-oxadiazo-5-yl]benzene,
tris(2,4,6-trimethyl-3-(pyridin-3-yl)phenyl)borane,
1-methyl-2-(4-(naphthalen-2-yl)phenyl)-1H-imidazo[4,5f]-[1,10]phenanthroline,
2-(naphthalen-2-yl)-4,7-diphenyl-1,10-phenanthroline, phenyldipyrenylphosphine oxide,
3,3',5,5'-tetra[(m-pyridyl)phen-3-yl]biphenyl,
1,3,5-tris[3-pyridyl]phen-3-yl]benzene,
4,4'-bis(4,6-diphenyl-1,3,5-triazin-2-yl)biphenyl,
1,3-bis[3,5-di(pyridin-3-yl)phenyl]benzene,
bis(10-hydroxybenzo[h]quinolinato) beryllium,
diphenylbis(4-(pyridin-3-yl)phenyl)silane and
3,5-di(pyren-1-yl)pyridine.

Illustrative examples of electron injection layer-forming materials include lithium oxide ($Li_2O$), magnesium oxide (MgO), alumina ($Al_2O_3$), lithium fluoride (LiF), sodium fluoride (NaF), magnesium fluoride ($MgF_2$), cesium fluoride (CsF), strontium fluoride ($SrF_2$), molybdenum trioxide ($MoO_3$), aluminum, Li(acac), lithium acetate and lithium benzoate.

Illustrative examples of negative electrode materials include aluminum, magnesium-silver alloys, aluminum-lithium alloys, lithium, sodium, potassium and cesium.

An example of an electron-blocking layer-forming material is tris(phenylpyrazole) iridium.

The method of fabricating polymer LED (PLED) devices using the charge-transporting varnish of the invention, although not particularly limited, is exemplified by the following method.

A PLED device having a charge-transporting thin-film formed with the charge-transporting varnish of the invention can be fabricated by, in the fabrication of an OLED device as described above, forming a hole transporting polymer layer and a light-emitting polymer layer instead of carrying out vacuum deposition operations for a hole transport layer, an emissive layer, an electron transport layer and an electron injection layer.

Specifically, the charge-transporting varnish of the invention is coated onto a positive electrode substrate and a hole injection layer is produced by the above-described method. A hole-transporting polymer layer and a light-emitting polymer layer are then successively formed on top thereof, in addition to which a negative electrode is vapor-deposited, thereby forming the PLED device.

The negative electrode and positive electrode materials used here may be similar to those used when fabricating an OLED device as described above, and similar cleaning treatment and surface treatment may be carried out.

The method of forming the hole-transporting polymer layer and the light-emitting polymer layer is exemplified by a film-forming method in which a hole-transporting polymer material or a light-emitting polymer material, or a material obtained by adding to either of these a dopant substance, is dissolved or uniformly dispersed by the addition of a solvent, following which the resulting solution or dispersion is coated onto the hole injection layer or hole-transporting polymer layer, and each is subsequently baked.

Illustrative examples of hole-transporting polymer materials include
poly[(9,9-dihexylfluorenyl-2,7-diyl)-co-(N,N'-bis{p-butylphenyl}-1,4-diaminophenylene)],
poly[(9,9-dioctylfluorenyl-2,7-diyl)-co-(N,N'-bis{p-butylphenyl}-1,1'-biphenylene-4,4-diamine)],
poly[(9,9-bis{1'-penten-5'-yl}fluorenyl-2,7-diyl)-co-(N,N'-bis{p-butylphenyl}-1,4-diaminophenylene)],
poly[N,N'-bis(4-butylphenyl)-N,N'-bis(phenyl)benzidine] end-capped with polysilsesquioxane and
poly[(9,9-dioctylfluorenyl-2,7-diyl)-co-(4,4'-(N-(p-butylphenyl))diphenylamine)].

Illustrative examples of light-emitting polymer materials include polyfluorene derivatives such as poly(9,9-dialkylfluorene) (PDAF), poly(phenylene vinylene) derivatives such as poly(2-methoxy-5-(2'-ethylhexoxy)-1,4-phenylene vinylene) (MEH-PPV), polythiophene derivatives such as poly(3-alkylthiophene) (PAT), and polyvinylcarbazole (PVCz).

Illustrative examples of the solvent include toluene, xylene and chloroform. Examples of the method of dissolution or uniform dispersion include stirring, stirring under applied heat, and ultrasonic dispersion.

Examples of the coating method include, but are not particularly limited to, inkjet printing, spraying, dipping, spin coating, transfer printing, roll coating and brush coating. Coating is preferably carried out in an inert gas atmosphere such as nitrogen or argon.

Examples of the baking method include methods that involve heating in an oven or on a hot plate and within an inert gas atmosphere or in a vacuum.

In addition, given that not only charge-transporting thin-films obtained from the above-described charge-transporting varnishes, but also vapor-deposited films obtained from the triphenylamine derivatives of the invention have excellent charge transportability, depending on the intended application, use can be made of a charge-transporting thin-film obtained by a vapor deposition process.

EXAMPLES

Synthesis Examples and Working Examples are given below to more concretely illustrate the invention, although the invention is not limited by these Examples. The equipment used was as follows.
(1) $^1$H-NMR Measurement:
 JNM-ECP300 FT NMR System, from JEOL, Ltd.
(2) Substrate Cleaning:
 Substrate cleaning machine (reduced-pressure plasma system), from Choshu Industry Co., Ltd.
(3) Varnish Coating:
 MS-A100 Spin Coater, from Mikasa Co., Ltd.

(4) Film Thickness Measurement:
 Surfcorder ET-4000 microfigure measuring instrument, from Kosaka Laboratory, Ltd.
(5) EL Device Fabrication:
 C-E2L1G1-N Multifunction Vapor Deposition System, from Choshu Industry Co., Ltd.
(6) Measurement of EL Device Brightness, etc.:
 I-V-L Measurement System from Tech World, Inc.
(7) EL Device Lifetime Measurement (half-life measurement):
 PEL-105S Organic EL Brightness Life Evaluation System, from EHC K.K.

[1] Synthesis of Compounds

[Synthesis Example 1] Synthesis of Arylsulfonic Acid Compound A

The Arylsulfonic Acid Compound A (formula (11)) used in the Examples was synthesized by the following reaction, based on the description provided in International Disclosure WO 2006/025342.

[Chemical Formula 10]

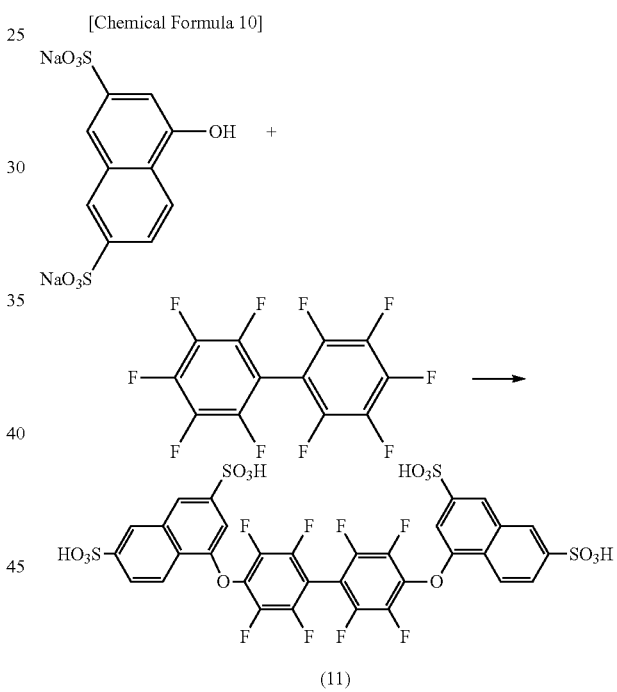

(11)

That is, 4.797 g (14.36 mol) of perfluorobiphenyl, 4.167 g (30.15 mol) of potassium carbonate and 100 mL of N,N-dimethylformamide were successively added to 11 g (31.59 mmol) of thoroughly dried sodium 1-naphthol-3,6-disulfonate and the reaction system was flushed with nitrogen, following which six hours of stirring was carried out at an internal temperature of 100° C.

The system was allowed to cool to room temperature, then an additional 500 mL of N,N-dimethylformamide was added and 90 minutes of stirring was carried out at room temperature in order to re-dissolve the Arylsulfonic Acid Compound A that had precipitated out following the reaction. After stirring at room temperature, this solution was filtered to remove the potassium carbonate residue, and was concentrated under reduced pressure. In addition, to remove remaining impurities, 100 mL of methanol was added to the residue and room temperature stirring was carried out. After 30 minutes of stirring at room temperature, the suspension was filtered, giving a residue. The residue was then dissolved by adding thereto 300 mL of ultrapure water, and the resulting solution was ion-exchanged by column chromatography using Dowex 650C cation-exchange resin (from Dow Chemical; about 200 mL of H-type; distillation solvent: ultrapure water).

The fraction at or below pH 1 was concentrated to dryness in vacuo and the residue was dried to hardness in vacuo, giving 11 g of a yellow powder (yield, 85%).

$^1$H-NMR (300 MHz, DMSO-d6):

δ 7.18 (1H, s, Ar—H), 7.89 (1H, d, Ar—H), 8.01 (1H, s, Ar—H), 8.23 (1H, s, Ar—H), 8.28 (1H, d, Ar—H)

Synthesis Example 2

The 4'-bromo-N-phenyl-[1,1'-biphenyl]-4-amine (formula (12)) used in Synthesis Example 3 was synthesized by the following reaction.

[Chemical Formula 11]

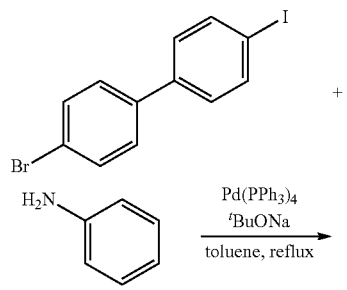

[Chemical Formula 12]

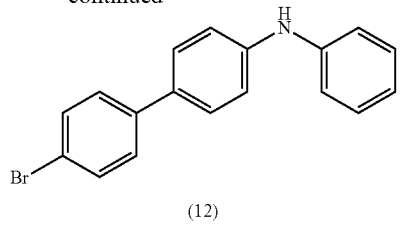

(12)

A flask was charged with 20 g of 4-bromo-4'-iodo-1,1'-biphenyl, 3.2 g of tetrakis(triphenylphosphine)palladium and 6.4 g of sodium t-butoxide and flushed with nitrogen, following which 200 mL of toluene and 6.1 g of aniline were added and stirring was carried out for 6.5 hours under refluxing conditions. The system was allowed to cool to room temperature, after which ion-exchanged water and chloroform were added and liquid-liquid extraction was carried out. The resulting organic phase was dried over sodium sulfate and then concentrated. The resulting residue was dissolved by adding chloroform thereto, then was separated and purified by column chromatography. The fractions containing the target substance were collected and concentrated. The powder thus obtained was re-crystallized, giving 11 g of 4'-bromo-N-phenyl-[1,1'-biphenyl]-4-amine.

$^1$H-NMR (300 MHz, CDCl$_3$):

δ 7.53-7.40 (m, 6H), 7.32-7.26 (m, 2H), 7.11 (d, d=8.6 Hz, 4H), 6.99-6.94 (t, d=7.4 Hz, 1H), 5.78 (s, 1H)

Synthesis Example 3

Triphenylamine Derivative B (formula (13)) used in the Examples was synthesized by the following reaction.

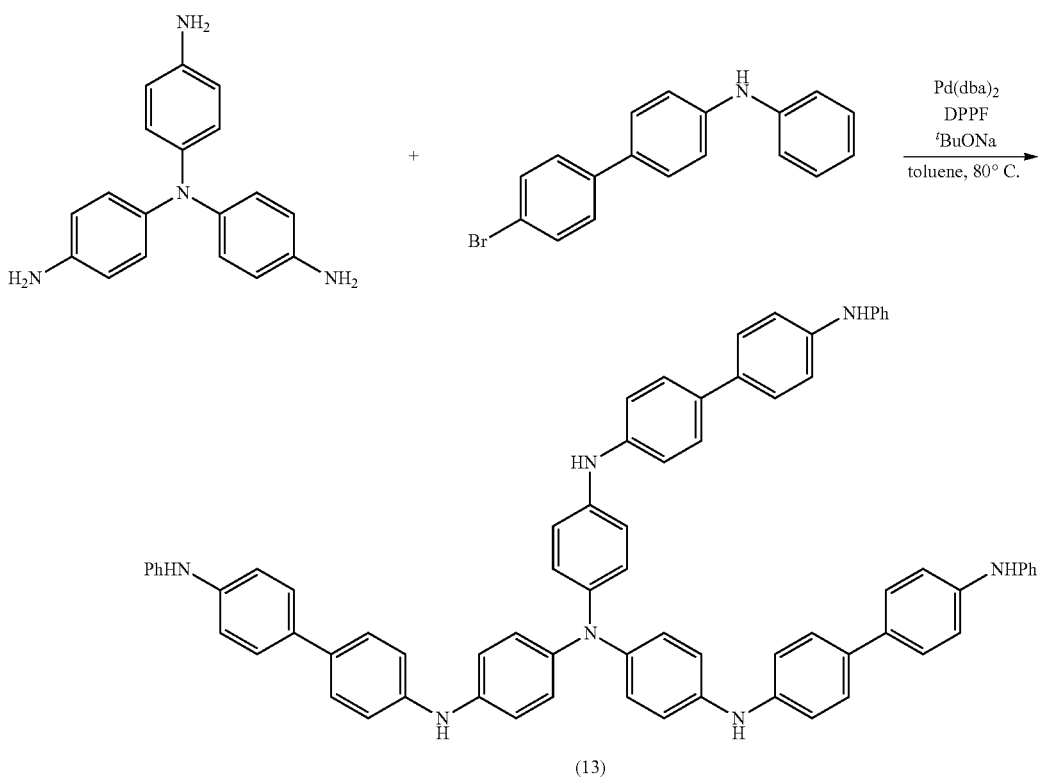

(13)

A flask was charged with 0.81 g of tris(4-aminophenyl)-amine, 3.0 g of 4'-bromo-N-phenyl-[1,1'-biphenyl]-4-amine, 0.24 g of bis(dibenzylideneacetone) palladium, 0.35 g of 1,1'-bis(diphenylphosphino)ferrocene (DPPF) and 1.1 g of sodium t-butoxide, then flushed with nitrogen, after which 73 mL of toluene was added and stirring was carried out for 5 hours at 80° C. The system was allowed to cool to room temperature, and then was filtered. The residue thus obtained was dissolved in THF, the solution was filtered to remove impurities, and the resulting filtrate was concentrated. The residue was dissolved by adding 15 mL of THF thereto, and 2.6 g of the target triphenylamine derivative was obtained by re-precipitation.

$^1$H-NMR (300 MHz, DMSO-d6):

δ 8.18 (s, 3H), 8.09 (s, 3H), 7.49-7.45 (m, 12H), 7.25-7.20 (m, 6H), 7.12-7.04 (m, 24H), 6.94 (d, d=8.6, 6H), 6.81 (t, d=7.1 Hz, 3H).

[2] Preparation of Charge-Transporting Varnish

Example 1-1

Triphenylamine Derivative B (0.074 g) and 0.297 g of phosphotungstic acid (abbreviated below as "PTA") were dissolved in 4 g of 1,3-dimethyl-2-imidazolidinone (abbreviated below as "DMI") under a nitrogen atmosphere. Cyclohexanol (6 g; abbreviated below as "CHA") and 2 g of propylene glycol (abbreviated below as "PG") were added to the resulting solution and stirring was carried out, thereby preparing a charge-transporting varnish.

Examples 1-2 to 1-4

Aside from setting the amounts in which Triphenylamine Derivative B and PTA were used to, respectively, 0.620 g and 0.309 g (Example 1-2), 0.053 g and 0.318 g (Example 1-3), and 0.034 g and 0.337 g (Example 1-4), charge-transporting varnishes were prepared in the same way as in Example 1-1.

Example 1-5

Triphenylamine Derivative B (0.210 g) and 0.279 g of Arylsulfonic Acid Compound A were dissolved in 8 g of DMI under a nitrogen atmosphere. CHA (12 g) and 4 g of PG were added to the resulting solution and stirring was carried out, thereby preparing a charge-transporting varnish.

Example 1-6

Triphenylamine Derivative B (0.123 g) and 0.245 g of Arylsulfonic Acid Compound A were dissolved in 6 g of DMI under a nitrogen atmosphere. CHA (9 g) and 3 g of PG were added to the resulting solution and stirring was carried out, thereby preparing a charge-transporting varnish.

Examples 1-7 and 1-8

Aside from setting the amounts in which Triphenylamine Derivative B and Arylsulfonic Acid Compound A were used to, respectively, 0.101 g and 0.267 g (Example 1-7), and 0.085 g and 0.282 g (Example 1-8), charge-transporting varnishes were prepared in the same way as in Example 1-6.

Examples 1-9

Triphenylamine Derivative B (0.124 g) and 0.619 g of PTA were dissolved in 8 g of DMI under a nitrogen atmosphere. CHA (12 g) and 4 g of PG were added to the resulting solution and stirring was carried out, after which 0.022 g of pentafluorophenyltriethoxysilane was added and further stirring was carried out, thereby preparing a charge-transporting varnish.

Example 1-10

Aside from using 0.025 g of 3,3,3-trifluoropropyltrimethoxysilane and 0.049 g of phenyltrimethoxysilane instead of 0.022 g of pentaphenyltriethoxysilane, a charge-transporting varnish was prepared in the same way as in Example 1-9.

[3] Fabrication of Organic EL Devices and Evaluation of Device Characteristics

Example 2-1

The varnish obtained in Example 1-1 was coated onto an ITO substrate using a spin coater, then dried at 50° C. for 5 minutes and baked in an open-air atmosphere at 230° C. for 10 minutes, thereby forming a uniform 30 nm thin-film on the ITO substrate. A 25 mm×25 mm×0.7 mm (t) glass substrate with indium-tin oxide (ITO) patterned on the surface to a film thickness of 150 nm was used as the ITO substrate. Prior to use, impurities on the surface were removed with an $O_2$ plasma cleaning system (150 W, 30 seconds).

Next, using a vapor deposition system (degree of vacuum, $1.0×10^{-5}$ Pa), thin-films of N,N'-di(1-naphthyl)-N,N'-diphenylbenzidine (α-NPD), tris(8-quinolinolate)aluminum(III) ($Alq_3$), lithium fluoride and aluminum were successively deposited on the ITO substrate on which a thin-film had been formed, thereby giving an organic EL device. Vapor deposition was carried out at a rate of 0.2 nm/s for α-NPD, $Alq_3$ and aluminum, and at a rate of 0.02 nm/s for lithium fluoride. The film thicknesses were set to, respectively, 30 nm, 40 nm, 0.5 nm and 120 nm.

To prevent the device characteristics from deteriorating due to the influence of oxygen, moisture and the like in air, the organic EL device was sealed with sealing substrates, after which the characteristics were evaluated. Sealing was carried out by the following procedure.

The organic EL device was placed between sealing substrates in a nitrogen atmosphere having an oxygen concentration of not more than 2 ppm and a dew point of not more than −85° C., and the sealing substrates were laminated together using an adhesive (XNR5516Z-B1, from Nagase ChemteX Corporation). A desiccant (HD-071010W-40, from Dynic Corporation) was placed, together with the organic EL device, within the sealing substrates at this time.

The laminated sealing substrates were irradiated with UV light (wavelength, 365 nm; dosage, 6,000 mJ/cm$^2$), then annealed at 80° C. for 1 hour to cure the adhesive.

Examples 2-2 to 2-8

Aside from using the varnishes obtained in Examples 1-2 to and 1-8 instead of the varnish obtained in Example 1-1, organic EL devices were fabricated in the same way as in Example 2-1.

Example 2-9

Aside from baking at 150° C. for 10 minutes instead of baking at 230° C. for 10 minutes, an organic EL device was fabricated in the same way as in Example 2-1.

Examples 2-10 to 2-13

Aside from using the charge-transporting varnishes obtained in Examples 1-2, 1-3, 1-9 and 1-10 instead of the varnish obtained in Example 1-1, organic EL devices were fabricated in the same way as in Example 2-9.

The current densities and brightnesses of the devices fabricated in each of the above Examples were measured at a driving voltage of 5 V. The results are shown in Table 1. As shown in Table 1, when a charge-transporting varnish according to the invention was used, EL devices having excellent brightness characteristics were obtained, not only when baked at a relatively high temperature of 230° C., but even when baked at a relatively low temperature of about 150° C.

TABLE 1

| | Charge-transporting varnish | Baking temperature | Current density (mA/cm$^2$) | Brightness (cd/m$^2$) | Current efficiency (cd/A) |
|---|---|---|---|---|---|
| Example 2-1 | Example 1-1 | 230° C. | 80 | 2,223 | 2.8 |
| Example 2-2 | Example 1-2 | 230° C. | 86 | 2,371 | 2.8 |
| Example 2-3 | Example 1-3 | 230° C. | 86 | 2,359 | 2.8 |
| Example 2-4 | Example 1-4 | 230° C. | 73 | 2,054 | 2.8 |
| Example 2-5 | Example 1-5 | 230° C. | 120 | 3,280 | 2.7 |
| Example 2-6 | Example 1-6 | 230° C. | 67 | 2,001 | 3.0 |
| Example 2-7 | Example 1-7 | 230° C. | 67 | 2,030 | 3.0 |
| Example 2-8 | Example 1-8 | 230° C. | 62 | 1,788 | 2.9 |
| Example 2-9 | Example 1-1 | 150° C. | 80 | 2,299 | 2.9 |
| Example 2-10 | Example 1-2 | 150° C. | 87 | 2,546 | 2.9 |
| Example 2-11 | Example 1-3 | 150° C. | 87 | 2,525 | 2.9 |
| Example 2-12 | Example 1-9 | 150° C. | 179 | 4,609 | 2.6 |
| Example 2-13 | Example 1-10 | 150° C. | 157 | 3,873 | 2.5 |

Durability tests (for measuring lifetime) were carried out on the devices fabricated in Examples 2-1 to 2-6 and 2-9. Table 2 shows the brightness half-lives (initial brightness, 5,000 cd/m$^2$). As shown in Table 2, organic EL devices provided with charge-transporting thin-films obtained from the charge-transporting varnishes of the invention had excellent durabilities.

TABLE 2

| | Half-life (hours) |
|---|---|
| Example 2-1 | 355 |
| Example 2-2 | 335 |
| Example 2-3 | 358 |
| Example 2-4 | 207 |
| Example 2-5 | 197 |
| Example 2-6 | 181 |
| Example 2-9 | 240 |

The invention claimed is:
1. A triphenylamine derivative characterized by having formula (1)

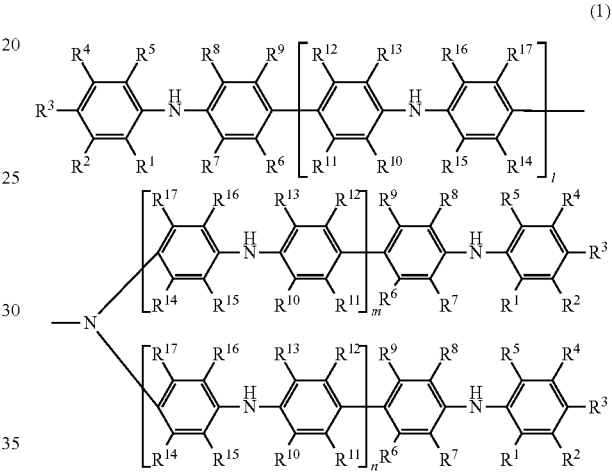

wherein
R$^1$ to R$^{17}$ are each independently a hydrogen atom, a halogen atom, a nitro group, a cyano group, an amino group, an aldehyde group, a hydroxyl group, a thiol group, a carboxyl group, an alkyl group of 1 to 20 carbons which may be substituted with Z$^1$, an alkenyl group of 2 to 20 carbons which may be substituted with Z$^1$, an alkynyl group of 2 to 20 carbons which may be substituted with Z$^1$, an aryl group of 6 to 20 carbons which may be substituted with Z$^2$, a heteroaryl group of 2 to 20 carbons which may be substituted with Z$^2$, —NHY$^1$, —NY$^2$Y$^3$, —C(O)Y$^4$, —OY$^5$, —SY$^6$, —C(O)OY$^7$, —OC(O)Y$^8$, —C(O)NHY$^9$ or —C(O)NY$^{10}$Y$^{11}$, Y$^1$ to Y$^{11}$ are each independently an alkyl group of 1 to 20 carbons which may be substituted with Z$^1$, an alkenyl group of 2 to 20 carbons which may be substituted with Z$^1$, an alkynyl group of 2 to 20 carbons which may be substituted with Z$^1$, an aryl group of 6 to 20 carbons which may be substituted with Z$^2$, or a heteroaryl group of 2 to 20 carbons which may be substituted with Z$^2$, in which Z$^1$ is a halogen atom, a nitro group, a cyano group, an amino group, an aldehyde group, a hydroxyl group, a thiol group, a sulfonic acid group, a carboxyl group, an aryl group of 6 to 20 carbons which may be substituted with Z$^3$, or a heteroaryl group of 2 to 20 carbons which may be substituted with Z$^3$;

$Z^2$ is a halogen atom, a nitro group, a cyano group, an amino group, an aldehyde group, a hydroxyl group, a thiol group, a sulfonic acid group, a carboxyl group, an alkyl group of 1 to 20 carbons which may be substituted with $Z^3$, an alkenyl group of 2 to 20 carbons which may be substituted with $Z^3$, or an alkynyl group of 2 to 20 carbons which may be substituted with $Z^3$;

$Z^3$ is a halogen atom, a nitro group, a cyano group, an amino group, an aldehyde group, a hydroxyl group, a thiol group, a sulfonic acid group or a carboxyl group; and the letters l, m, and n are each independently integers from 1 to 5.

2. The triphenylamine derivative of claim 1, wherein $R^1$ to $R^{17}$ are all hydrogen atoms.

3. A charge-transporting substance consisting of the triphenylamine derivative of claim 1 or 2.

4. A charge-transporting material comprising the charge-transporting substance of claim 3.

5. A charge-transporting varnish comprising the charge-transporting substance of claim 3, a dopant substance and an organic solvent.

6. A charge-transporting thin-film produced using the charge-transporting varnish of claim 5.

7. An electronic device comprising a positive electrode, the charge-transporting thin-film of claim 6 stacked on said positive electrode, and a hole transport layer or an emissive layer stacked on said charge-transporting thin-film.

8. An organic electroluminescence device comprising a positive electrode, the charge-transporting thin-film of claim 6 stacked on said positive electrode, and a hole transport layer or an emissive layer stacked on said charge-transporting thin-film.

9. A method of producing a charge-transporting thin-film, characterized by coating the charge-transporting varnish of claim 5 onto a substrate and evaporating off the solvent.

10. A method of producing the triphenylamine derivative of claim 1, comprising the step of reacting the triphenylamine compound of formula (2) with compounds having the diphenylamine structures of formulas (3) to (5)

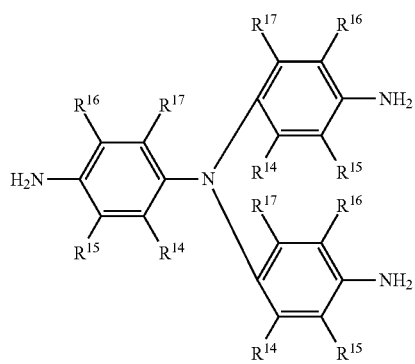

(2)

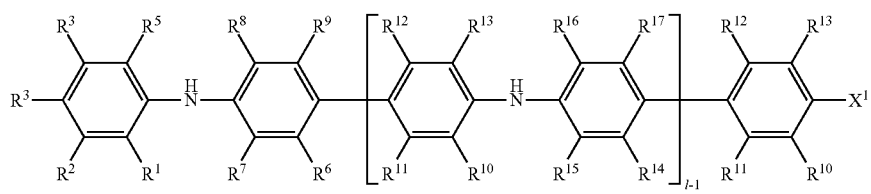

(3)

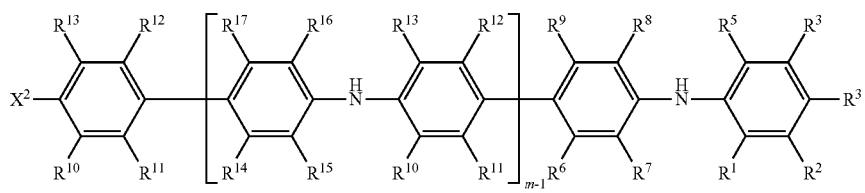

(4)

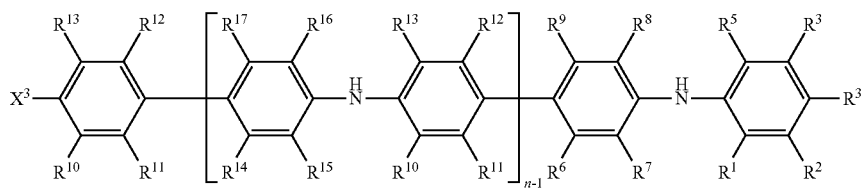

(5)

wherein $X^1$ to $X^3$ are each independently a halogen atom or a pseudo-halogen group, and $R^1$ to $R^{17}$ and the letters l, m and n are as defined above in the presence of a catalyst.

* * * * *